US011680105B2

(12) United States Patent
Panyam et al.

(10) Patent No.: US 11,680,105 B2
(45) Date of Patent: Jun. 20, 2023

(54) ANTIBODY FRAGMENTS FOR DETECTING CANCER AND METHODS OF USE

(71) Applicant: REGENTS OF THE UNIVERSITY OF MINNESOTA, Minneapolis, MN (US)

(72) Inventors: Jayanth Panyam, Minneapolis, MN (US); Stephen Kalscheuer, Minneapolis, MN (US); Vidhi D. Khanna, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 426 days.

(21) Appl. No.: 16/745,153

(22) Filed: Jan. 16, 2020

(65) Prior Publication Data

US 2020/0332020 A1    Oct. 22, 2020

Related U.S. Application Data

(60) Provisional application No. 62/793,726, filed on Jan. 17, 2019.

(51) Int. Cl.
*A61K 47/68* (2017.01)
*A61P 35/00* (2006.01)
*A61K 39/00* (2006.01)
*C07K 16/30* (2006.01)

(52) U.S. Cl.
CPC ...... *C07K 16/3015* (2013.01); *A61K 47/6803* (2017.08); *A61K 47/6855* (2017.08); *A61P 35/00* (2018.01); *A61K 2039/505* (2013.01); *C07K 2317/56* (2013.01); *C07K 2317/622* (2013.01); *C07K 2319/00* (2013.01)

(58) Field of Classification Search
CPC .............. A61K 47/00; A61K 47/6855; A61K 47/6803; A61K 47/6843; A61K 47/6889; A61K 47/6937; A61K 49/00; A61K 49/0032; A61K 49/0058; A61K 2039/505; C07K 16/3015; C07K 16/28; C07K 16/30; C07K 2317/56; C07K 2317/622; C07K 2319/00; C07K 2317/21; C07K 2317/41; C07K 2317/565; C07K 2317/73; C07K 2317/732; C07K 2317/90; C07K 2317/92; A61P 35/00
USPC .......... 424/1.11, 1.65, 1.69, 1.81, 1.85, 1.89, 424/9.1, 9.2, 1.49; 530/300; 514/1, 1.1
See application file for complete search history.

(56) References Cited

U.S. PATENT DOCUMENTS

| | | | |
|---|---|---|---|
| 3,773,919 A | 11/1973 | Boswell et al. | |
| 4,816,567 A | 3/1989 | Cabilly et al. | |
| 4,873,192 A | 10/1989 | Kunkel | |
| 4,946,778 A | 8/1990 | Ladner et al. | |
| 5,091,513 A | 2/1992 | Huston et al. | |
| 5,260,203 A | 11/1993 | Ladner et al. | |
| 5,455,030 A | 10/1995 | Ladner et al. | |
| 6,432,636 B1 | 8/2002 | Maresh et al. | |
| 8,501,418 B2 | 8/2013 | Kas et al. | |
| 10,166,304 B2* | 1/2019 | Panyam | G01N 33/57415 |
| 2008/0248050 A1 | 10/2008 | Stevens | |
| 2010/0008937 A1 | 1/2010 | Peer et al. | |
| 2012/0034240 A1 | 2/2012 | Kas et al. | |

FOREIGN PATENT DOCUMENTS

| | | |
|---|---|---|
| CN | 102936598 B | 4/2014 |
| EP | 0058481 A1 | 8/1982 |
| EP | 0133988 A2 | 3/1985 |
| EP | 0239400 A2 | 9/1987 |
| EP | 0404097 A2 | 12/1990 |
| WO | 1993011161 A1 | 6/1993 |
| WO | 1996002576 A1 | 2/1996 |
| WO | 2013040188 A1 | 3/2013 |

OTHER PUBLICATIONS

Morrison, et al., "Chimeric human antibody molecules: Mouse antigen-binding domains with human constant region domains", Proc. Natl. Acad. Sci. USA 8I, 6851-6855 (1984).
Murdoch, A, et al., "Widespread Expression of Perlecan Proteoglycan in Basement Membranes adn Extracellular Matrices of Human Tissues as Detected by a Novel Monoclonal Antibody Against Domain III and by In Situ Hybridization", Journal of Histochemistry and Cytochemistry 42(2), 239-249 (1994).
Myers, E, et al., "Optimal alignments in linear space", CABIOS 4(1), 11-17 (1988).
Needleman, S, et al., "A General Method Applicable to the Search for Similarities in the Amino Acid Sequence of Two Proteins", J Mol Biol 48, 443-453 (1970).
Ohtsuka, E, et al., "An Alternative Approach to Deoxyoligonucleotides as Hybridization Probes by Insertion of Deoxyinosine at Ambiguous Codon Positions", JBC 260(5), 2605-2608 (1985).
Pantel, K., et al., "Detection and clinical implications of early systemic tumor cell dissemination in breast cancer", Clin Cancer Res. 9(17), 6326-6334 (2003).
Patani, N., et al., "Clinical significance of sentinel lymph node isolated tumour cells in breast cancer", Breast Cancer Res Treat. 127(2), 325-334 (2011).
Pearson, W, et al., "Improved tools for biological sequence comparison", Proc Natl Acad Sci 85, 2444-2448 (1988).
Pearson, W, et al., "Using the FASTA program to search protein and DNA sequence databases.", Meth Mol Biol 24, 307-331 (1994).
Presta, L, "Antibody engineering", Curr. Op. Struct. Biol. vol. 2, 593-596 (1992).

(Continued)

Primary Examiner — D. L. Jones
(74) Attorney, Agent, or Firm — Viksnins Harris Padys Maien LLP

(57) ABSTRACT

The present invention relates to diagnostic and therapeutic agents comprising recombinant antibody fragments to bind a protein associated with cancer and methods of use of these diagnostic and therapeutic agents.

19 Claims, 25 Drawing Sheets
(22 of 25 Drawing Sheet(s) Filed in Color)
Specification includes a Sequence Listing.

(56) References Cited

OTHER PUBLICATIONS

Reichmann, L , et al., "Reshaping human antibodies for therapy", Nature 332(6162), 323-327 (1988).
Rosenburg, M , et al., "The Pharmacology of Monoclonal Antibodies. Chapter 11 Antibodies from *Escherichia coli*", Springer Verlag, NY , Chapter 11, vol. 113, 269-315 (1994).
Rossolini, G , et al., "Use of deoxyinosine-containing primers vs degenerate primers for polymerase chain reaction based on ambiguous sequence information", Mol Cell Probes 8, 91-98 (1994).
Sato , et al., "Reshaping a Human Antibody to Inhibit the Interleukin 6-dependent Tumor Cell Growth", Cancer Res. 53, 851-856 (1993).
Sidman, K , et al., "Controlled Release of Macromolecules and Pharmaceuticals from Synthetic Polypeptides Based an Glutamic Acid", Biopolymers 22, 547-556 (1983).
Smith, T , et al., "Comparison of biosequences", Adv Appl Math 2(4), 482-489 (1981).
Trumpp, A., et al., "Mechanisms of Disease: cancer stem cells—targeting the evil twin", Nat Clin Pract Oncol. 5(6), 337-347 (2008).
Tsuji, T. , et al., "Epithelial-mesenchymal transition induced by growth suppressor p12CDK2-AP1 promotes tumor cell local invasion but suppresses distant colony growth", Cancer Res. 68(24), 10377-10386 (2008).
Turner, R , et al., "The potential exploitation of plant viral translational enhancers in biotechnology for increased gene expression.", Mol Biotech 3(3), 225-236 (1995).
Wang, A., et al., "Site-specific mutagenesis of the human interleukin-2 gene: structure-function analysis of the cysteine residues", Science 224(4656), 1431-1433 (1984).
Waterhouse , et al., "Combinatoial infection and in vivo recombination: a strategy for making large phage antibody repertoires", Nucleic Acids Res 21 (9), 2265-2266 (1993).
Xu, R., et al., "Gene transcriptional networks integrate microenvironmental signals in human breast cancer", Integr Biol. 3(4), 368-374(2011).
Yang, J., et al., "Exploring a new twist on tumor metastasis", Cancer Res. 66(9), 4549-4552 (2006).
Zoller, M , et al., "Oligonucleotide-directed mutagenesis using M13-derived vectors: an efficient and general procedure for the production of point mutations in any fragment of DNA", Nucleic Acids Res 10(20), 6487-6500 (1982).
Adams, G , et al., "Prolonged in vivo tumour retention of a human diabody targeting the extracellular domain of human HER2/neu", British Journal of Cancer 77(9), 1405-1412 (1998).
Aktas, B. , et al., "Stem cell and epithelial-mesenchymal transition markers are frequently overexpressed in circulating tumor cells of metastatic breast cancer patients", Breast Cancer Res. 11(4), R46 (2009).
Altschul, S , et al., "Basic local alignment search tool", J Mol Biol 215, 403-410 (1990).
Altschul, S , et al., "Gapped BLAST and PSI-BLAST: a new generation of protein database search programs.", Nucleic Acids Res 25(17), 3389-3402 (1997).
American Cancer Society , Cancer Facts and Figures, 72 pages (2014).
Anderl, J , et al., "Antibody-drug conjugate payloads", Methods Mol Biol. 1045, 51-70 (2013).
Batzer, M , et al., "Enhanced evolutionary PCR using oligonucleotides with inosine at the 3'-terminus", Nucl Acids Res 19(18), 5081 (1991).
Behrens, C , et al., "Methods for site-specific drug conjugation to antibodies", MAbs. 6(1), 46-53 (2014).
Better, M , et al., "Expression of engineered antibodies and antibody fragments in microorganisms", Methods in Enzymology 178, 476-496 (1989).
Bird , et al., "Single Chain Antibody Variable Regions", Tibtech 9, 132-137 (1991).
Bonnomet, A., et al., "Epithelial-to-mesenchymal transitions and circulating tumor cells", J Mammary Gland Biol Neoplasia. 15(2), 261-273 (2010).
Brabletz, T. , et al., "Migrating cancer stem cells—an integrated concept of malignant tumour progression", Nat Rev Dancer. 5(9), 744-749 (2005).
Brennan , et al., "Preparation of Bispecific Antibodies by Chemical Recombination of Monoclonal Immunoglobulin G1 Fragments", Science 229, 81-83 (1985).
Burgess, W , et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", Journal of Cell Biology 111, 2129-2138 (1990).
Carter, et al., "High Level *Escherichia coli* Expression and Production of a Bivalent Humanized Antibody Fragment", Bio/Technology 10, 163-167 (1992).
Christianson, H , et al., "ScFv anti-heparan sulfate antibodies unexpectedly activate endothelial and cancer cells through p38 MAPK: implications for antibody-based targeting of heparan sulfate proteoglycans in cancer", PLoS One 7 (11), e49092, 12 pages (2012).
Clackson, Tim , et al., "Making antibody fragments using phage display libraries", Nature 352, 624-628 (1991).
Co, M , et al., "A humanized antibody specific for the platelet integrin gpIIb/IIIa", J Immunol 152, 2968-2976 (1994).
Corpet, F , et al., "Multiple sequence alignment with hierarchical clustering", Nucl Acids Res 16, 10881-10890 (1988).
Dalbadie-McFarland, G., et al., "Oligonucleotide-directed mutagenesis as a general and powerful method for studies of protein function", Proc Natl Acad Sci 79(21), 6409-6413 (1982).
Dean, M. , et al., "Tumour stem cells and drug resistance", Nat Rev Cancer. 5(4), 275-284 (2005).
Ducry, L , "Antibody-Drug Conjugates", Methods in Molecular Biology, vol. 1045, 51-70 (2013).
Higgins, D , et al., "CLUSTAL: a package for performing multiple sequence alignment on a microcomputer", Gene 73, 237-244 (1988).
Higgins, D , et al., "Fast and sensitive multiple sequence alignments on a microcomputer.", CABIOS 5(2), 151-153 (1989).
Holliger , et al., ""Diabodies": Small bivalent and bispecific antibody fragments", Proc. Natl. Acad. Sci. 90, 6444-6448 (1993).
Huang, X , et al., "Parallelization of a local similarity algorithm", CABIOS 8,155-165 (1992).
Huston, J , et al., "Protein engineering of antibody binding sites: Recovery of specific activity in an anti-digoxin single-chain Fv analogue produced in *Escherichia coli*", Proc. Natl. Acad Sci. 85, 5879-5883 (1988).
Jones , et al., "Replacing the complementarity-determining regions in a human antibody with those from a mouse", Nature 321, 522-525 (1986).
Kallergi, G , et al., "Epithelial to mesenchymal transition markers expressed in circulating tumour cells of early and metastatic breast cancer patients", Breast Cancer Res. 13(3), R59 (2011).
Kalluri, R. , et al., "Fibroblasts in cancer", Nat Rev Cancer. 6(5), 392-401 (2006).
Kalscheuer, S , et al., "Discovery of HSPG2 (Perlecan) as a Therapeutic Target in Triple Negative Breast Cancer", Scientific Reports 9, 12492, 11 pages (2019).
Kalscheuer, S , "Humanized antibody development using phage display: applications to solid tumor metastasis", University of Minnesota Ph.D. dissertation, 1-128 (Jul. 2016).
Karlin, S , et al., "Applications and statistics for multiple high-scoring segments in molecular sequences", Proc Natl Acad Sci 90, 5873-5877 (1993).
Karlin, S , et al., "Methods for assessing the statistical significance of molecular sequence features by using general scoring schemes", Proc Natl Acad Sci 87(6), 2264-2268 (1990).
Khanna, V , et al., "Perlecan-targeted nanoparticles for drug delivery to triple-negative breast cancer", Future Drug Discov 1(1) eISSN 2631-3316, 12 pages (2019).
Kohler , et al., "Continuous cultures of fused cells secreting antibody of predefined specificity", Nature 256, 495-497 (1975).
Kunkel, T , "Rapid and efficient site specific mutagenesis without phenotypic selection", Proc. Natl Acad Sci vol. 82, 488-492 (1985).
Kunkel, T , et al., "Rapid and Efficient Site-Specific Mutagenesis without Phenotypic Selection", Meth Enzymol 154, 367-382 (1987).

(56) References Cited

OTHER PUBLICATIONS

Lamoyi, E , "Preparation of F(ab')2 fragments from mouse IgG of various subclasses", Methods Enzymol 121, 652-663 (1986).
Langer, R , et al., "Biocompatibility of polymeric delivery systems for macromolecules", J. Biomed. Mater. Res. 15, 267-277 (1981).
Langer, R , "Controlled release of macromolecules", Chem. Tech. 12, 98-105 (1982).
Lazar, E , et al., "Transforming Growth Factor alpha: Mutation of Aspartic Acid 47 and Leucine 48 Results in Different Biological Activites", Molecular and Cellular Biology 8(3), 1247-1252 (1988).
Malhotra, G , et al., "Histological, molecular and functional subtypes of breast cancers", Cancer Biol Ther. 10(10), 955-60 (2010).
Mark, D , et al., "Site-specific mutagenesis of the human fibroblast interferon gene", Proc Natl Acad Sci. 81(18), 5662-5666 (1984).
Marks , et al., "By-passing immunization. Human antibodies from V-gene libraries displayed on phage", J Mol Biol 222(3), 581-597 (1991).
Marks , et al., "By-Passing Immunization: Building High Affinity Human Antibodies by Chain Shuffling", Bio/Technology 10, 779-783 (1992).
McCafferty , et al., "Phage antibodies: filamentous phage displaying antibody variable domains", Nature 348, 552-554 (1990).
Meinkoth, J , et al., "Hybridization of nucleic acids immobilized on solid supports ", Anal Biochem 138(2), 267-284 (1984).
Millner, L , et al., "Circulating tumor cells: a review of present methods and the need to identify heterogeneous phenotypes", Ann Clin Lab Sci. 43(3), 295-304 (2013).
Morimoto , et al., "Single-step purification of F(ab')2 fragments of mouse monoclonal antibodies (immunoglobulins G1) by hydrophobic interaction high performance liquid chromatography using TSKgel Phenyl-5PW", Journal of Biochemical and Biophysical Methods 24, 107-117 (1992).

\* cited by examiner

Figure 8A

Tw1S4_AM6 Light Chain Full DNA

ATGTACAGGATGCAACTCCTGTCTTGCATTGCACTAAGTCTTGCACTTGTCACGAATTCAACGG
ACATCCAGATGACCCAGTCTCCATCCTCCCTGTCTGCATCTGTAGGAGACAGAGTCACCATCAC
TTGCCGGGCAAGTCAGAGCATTAGCAGCTATTTAAATTGGTATCAGCAGAAACCAGGGAAAGCC
CCTAAGCTCCTGATCTATAATGCATCCCTTTTGCAAAGTGGGGTCCCATCAAGGTTCAGTGGCA
GTGGATCTGGGACAGATTTCACTCTCACCATCAGCAGTCTGCAACCTGAAGATTTTGCAACTTA
CTACTGTCAACAGACCCGGAATCACCGCACCCACTTCGGCCAAGGGACCAAGGTGGAAATCAAA
CGGACGGTGGCTGCACCATCTGTCTTCATCTTCCCGCCATCTGATGAGCAGTTGAAATCTGGAA
CTGCCTCTGTTGTGTGCCTGCTGAATAACTTCTATCCCAGAGAGGCCAAAGTACAGTGGAAGGT
GGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACG
CCTGCGAAGTCACCCATCAGGGCCTGAGCTCGCCCGTCACAAAGAGCTTCAACAGGGGAGAGTG
TTAG (SEQ ID NO:13)

Amino Acids

▓▓▓▓▓▓▓▓▓▓▓▓▓▓▓▓ *TDIQMTQSPS SLSASVGDRV TITC*▓▓▓▓ ▓▓▓▓*NWYQQK*
    *PGKAPKLLIY* ▓▓▓▓▓*GVP SRFSGSGSGT DFTLTISSLQ PEDFATYYC*▓▓▓*TRNHRTHFG*
    *QGTKVEIKRT* ▓▓▓▓▓▓▓▓▓▓▓▓▓▓▓▓▓▓▓▓▓▓▓▓▓▓▓▓▓▓▓▓▓▓▓▓

(SEQ ID NO: 11)

▓▓  SECRETION TAG(SEQ ID NO:14), NOT PART OF ANTIBODY SEQUENCE
▓▓  (SEQ ID NO: 5)
▓▓  (SEQ ID NO: 6)
CDR3=▓▓ + ▓▓▓▓▓▓▓ (SEQ ID NO: 7)
▓▓▓▓▓▓▓▓▓▓▓▓ (SEQ ID NO: 17)
Variable region = *Italicized* (SEQ ID NO: 9)
Full-length antibody excluding secretion tag (SEQ ID NO: 21)

Figure 8B. Tw1S4_AM6 Heavy Chain Full DNA

ATGTACAGGATGCAACTCCTGTCTTGCATTGCACTAAGTCTTGCACTTGTCACGAATTCAGAGG
TGCAGCTGTTGGAGTCTGGGGGAGGCTTGGTACAGCCTGGGGGGTCCCTGAGACTCTCCTGTGC
AGCCTCTGGATTCACCTTTAGCAGCTATGCCATGAGCTGGGTCCGCCAGGCTCCAGGGAAGGGG
CTGGAGTGGGTCTCAGCGATTAGGGAGGATGGTATTAAGACATATTACGCAGACTCCGTGAAGG
GCCGGTTCACCATCTCCAGAGACAATTCCAAGAACACGCTGTATCTGCAAATGAACAGCCTGAG
AGCCGAGGACACGGCCGTATATTACTGTGCGAAAAGGGCTCGTCGGTTTGACTACTGGGGCCAG
GGAACCCTGGTCACCGTCTCGAGCGCTAGCACCAAGGGCCCATCGGTCTTCCCCCTGGCACCCT
CCTCCAAGAGCACCTCTGGGGGCACAGCGGCCCTGGGCTGCCTGGTCAAGGACTACTTCCCCGA
ACCGGTGACGGTGTCGTGGAACTCAGGCGCCCTGACCAGCGGCGTGCACACCTTCCCGGCTGTC
CTACAGTCCTCAGGACTCTACTCCCTCAGCAGCGTGGTGACCGTGCCCTCCAGCAGCTTGGGCA
CCCAGACCTACATCTGCAACGTGAATCACAAGCCCAGCAACACCAAGGTGGACAAGAAAGTTGA
GCCCAAATCTTGTGACAAAACTCACACATGCCCACCGTGCCCAGCACCTGAACTCCTGGGGGGA
CCGTCAGTCTTCCTCTTCCCCCCAAAACCCAAGGACACCCTCATGATCTCCCGGACCCCTGAGG
TCACATGCGTGGTGGTGGACGTGAGCCACGAAGACCCTGAGGTCAAGTTCAACTGGTACGTGGA
CGGCGTGGAGGTGCATAATGCCAAGACAAAGCCGCGGGAGGAGCAGTACAACAGCACGTACCGT
GTGGTCAGCGTCCTCACCGTCCTGCACCAGGACTGGCTGAATGGCAAGGAGTACAAGTGCAAGG
TCTCCAACAAAGCCCTCCCAGCCCCCATCGAGAAAACCATCTCCAAAGCCAAAGGGCAGCCCCG
AGAACCACAGGTGTACACCCTGCCCCCATCCCGGGAGGAGATGACCAAGAACCAGGTCAGCCTG
ACCTGCCTGGTCAAAGGCTTCTATCCCAGCGACATCGCCGTGGAGTGGGAGAGCAATGGGCAGC
CGGAGAACAACTACAAGACCACGCCTCCCGTGCTGGACTCCGACGGCTCCTTCTTCCTCTACAG
CAAGCTCACCGTGGACAAGAGCAGGTGGCAGCAGGGGAACGTCTTCTCATGCTCCGTGATGCAT
GAGGCTCTGCACAACCACTACACGCAGAAGAGCCTCTCCCTGTCTCCGGGTAAATGA (SEQ
ID NO:12)

Amino Acids

EVQLLESGGG LVQPGGSLRL SCAASGFTFS SYAMSWVRQA
PGKGLEW KGRFTI SRDNSKNTLY LQMNSLRAED TAVYYCAK
WGQGT LVTVSSA (SEQ ID NO: 10)

SECRETION TAG (SEQ ID NO: 14), NOT PART OF ANTIBODY SEQUENCE
CDR1 (SEQ ID NO: 2)
(SEQ ID NO: 3)
(SEQ ID NO: 4)
region (SEQ ID NO: 15)
Variable region = *Italicized* (SEQ ID NO: 8)
Full-length antibody excluding secretion tag (SEQ ID NO: 22)

Figure 9

TW1S4 Light Chain Full DNA

ATGTACAGGATGCAACTCCTGTCTTGCATTGCACTAAGTCTTGCACTTGTCACGAATTCAACGG
ACATCCAGATGACCCAGTCTCCATCCTCCCTGTCTGCATCTGTAGGAGACAGAGTCACCATCAC
TTGCCGGGCAAGTCAGAGCATTAGCAGCTATTTAAATTGGTATCAGCAGAAACCAGGGAAAGCC
CCTAAGCTCCTGATCTATAATGCATCCCTTTTGCAAAGTGGGGTCCCATCAAGGTTCAGTGGCA
GTGGATCTGGGACAGATTTCACTCTCACCATCAGCAGTCTGCAACCTGAAGATTTTGCAACTTA
CTACTGTCAACAGAGTCTGCGTTCGCCTATTACGTTCGGCCAAGGGACCAAGGTGGAAATCAAA
CGGACGGTGGCTGCACCATCTGTCTTCATCTTCCCGCCATCTGATGAGCAGTTGAAATCTGGAA
CTGCCTCTGTTGTGTGCCTGCTGAATAACTTCTATCCCAGAGAGGCCAAAGTACAGTGGAAGGT
GGATAACGCCCTCCAATCGGGTAACTCCCAGGAGAGTGTCACAGAGCAGGACAGCAAGGACAGC
ACCTACAGCCTCAGCAGCACCCTGACGCTGAGCAAAGCAGACTACGAGAAACACAAAGTCTACG
CCTGCGAAGTCACCCATCAGGGCCTGAGCTCGCCCGTCACAAAGAGCTTCAACAGGGGAGAGTG
TTAG (SEQ ID NO: 18)

Amino Acid

*TDIQMTQSPS SLSASVGDRV TITC*▓▓▓▓
▓▓▓▓*WYQQK PGKAPKLLIY* ▓▓▓▓*GVP SRFSGSGSGT DFTLTISSLQ*
*PEDFATYYC*▓ ▓▓▓▓▓▓*FG QGTKVEIKRT* ▓▓▓▓▓▓▓▓▓▓▓▓
▓▓▓▓▓▓▓▓▓▓▓▓▓▓▓▓▓▓▓▓▓▓▓▓ (SEQ ID NO: 19)

▓▓ SECRETION TAG(SEQ ID NO:14), NOT PART OF ANTIBODY SEQUENCE
▓▓ CDR1 (SEQ ID NO: 5)
▓▓ (SEQ ID NO: 6)
▓▓ CDR3 (SEQ ID NO: 16)
▓▓▓▓ region (SEQ ID NO: 17)
Variable region = *Italicized* (SEQ ID NO: 20)
Full-length antibody excluding secretion tag (SEQ ID NO: 23)

Figure 10

EMT = Tw1S4_AM6 hma and EASGGPE are linkers. hma (human muscle aldolase) is the linker between CD16 and IL15. EASGGPE (E=glutamic acid, A = alanine, S = serine, etc.) is the linker between IL15 and EMT EASGGPE (SEQ ID NO:24) = gaagcttccggaggtcccgag (SEQ ID NO:25)

hma = ccgtctggtcaggctggtgctgctgctagcgaatctctgttcgtttctaaccacgcttac (SEQ ID NO:26)

AM6 =
ATGGACGAGGTGCAGCTGTTGGAGTCTGGGGGAGGCTTGGTACAGCCTGGGGGGTCCCTGAGAC
TCTCCTGTGCAGCCTCTGGATTCACCTTTAGCAGCTATGCCATGAGCTGGGTCCGCCAGGCTCC
AGGGAAGGGGCTGGAGTGGGTCTCAGCGATTAGGGAGGATGGTATTAAGACATATTACGCAGAC
TCCGTGAAGGGCCGGTTCACCATCTCCAGAGACAATTCCAAGAACACGCTGTATCTGCAAATGA
ACAGCCTGAGAGCCGAGGACACGGCCGTATATTACTGTGCGAAAAGGGCTCGTCGGTTTGACTA
CTGGGGCCAGGGAACCCTGGTCACCGTCTtGAGCGGTGGAGGCGGTTCAGGCGGAGGTGGCAGC
GGCGGTGGCGGGTCGGACATCCAGATGACCCAGTCTCCATCCTCCCTGTCTGCATCTGTAGGAG
ACAGAGTCACCATCACTTGCCGGGCAAGTCAGAGCATTAGCAGCTATTTAAATTGGTATCAGCA
GAAACCAGGGAAAGCCCCTAAGCTCCTGATCTATAATGCATCCCTTTTGCAAAGTGGGGTCCCA
TCAAGGTTCAGTGGCAGTGGATCTGGGACAGATTTCACTCTCACCATCAGCAGTCTGCAACCTG
AAGATTTTGCAACTTACTACTGTCAACAGACCCGGAATCACCGCACCCACTTCGGCCAAGGGAC
CAAGGTGGAAATCAAACGG (SEQ ID NO:27) (lower case t (middle line 6) in AM6 sequence indicates silent mutation (ctc changed to ctt) to remove XhoI site)

2 stops and XhoI restriction site = TGATAGctcgag (SEQ ID NO:28)

Amino Acid sequence

Met D E V Q L L E S G G G L V Q P G G S L R L S C A A S G F T F
S S Y A Met S W V R Q A P G K G L E W V S A I R E D G I K T Y Y
A D S V K G R F T I S R D N S K N T L Y L Q Met N S L R A E D T
A V Y Y C A K R A R R F D Y W G Q G T L V T V L S G G G G S G G
G G S G G G S D I Q Met T Q S P S S L S A S V G D R V T I T C
R A S Q S I S S Y L N W Y Q Q K P G K A P K L L I Y N A S L L Q
S G V P S R F S G S G S G T D F T L T I S S L Q P E D F A T Y Y
C Q Q T R N H R T H F G Q G T K V E I K R (SEQ ID NO:1)

| Characteristics | Anti-perlecan-Az NP | Blank NP |
|---|---|---|
| Nanoparticle Size | 364.2 ± 24.8 nm | 337 ± 38.3 nm |
| Zeta Potential | -12.7 ± 2.7mV | -11.9 ± 3.6mV |
| Protein Loading | 7 ± 3 µg protein/mg NPs | - |
| Protein Encapsulation Efficiency | 75 ± 25 % | - |
| Paclitaxel Loading | 15.5% ± 1.7 | 15.1% ± 2.5 |

Figure 21
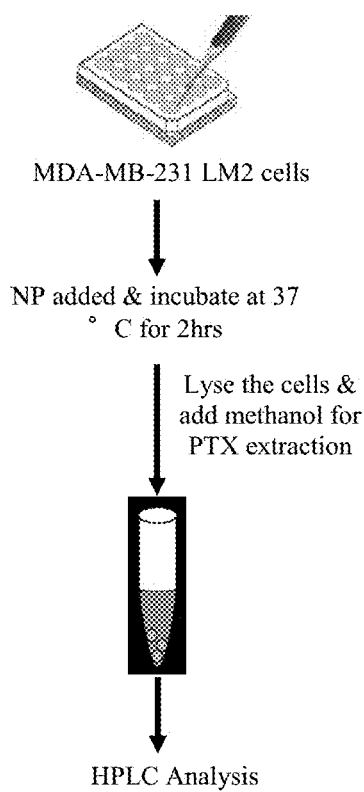
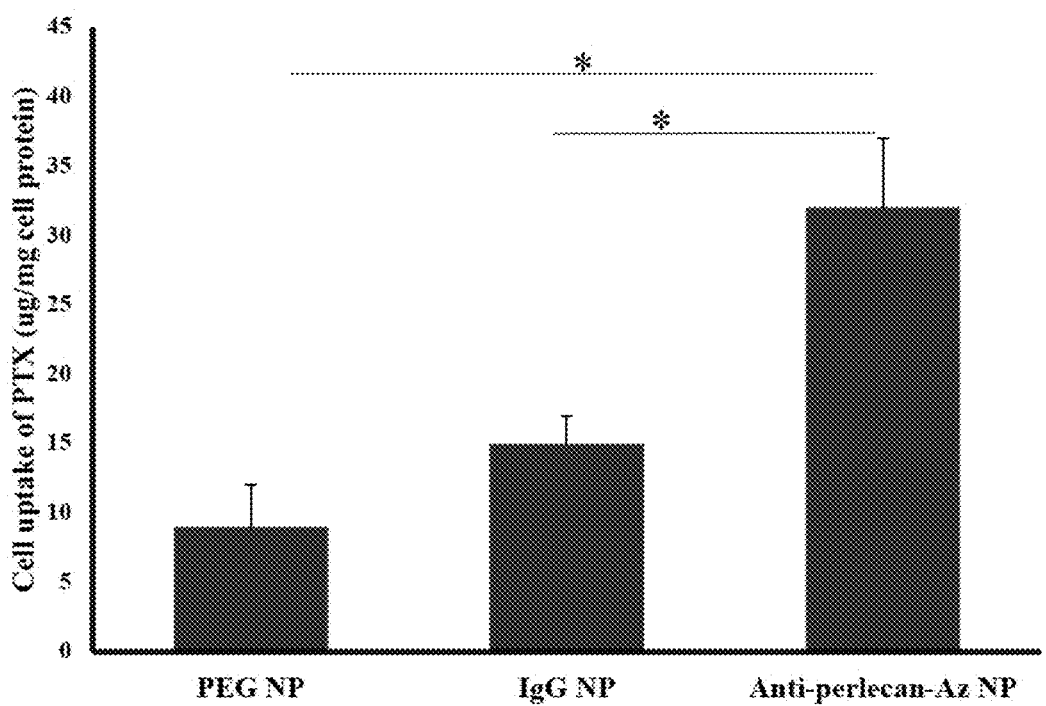

Figure 22
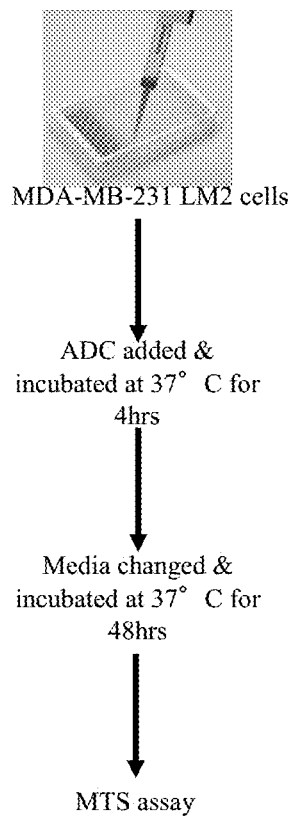
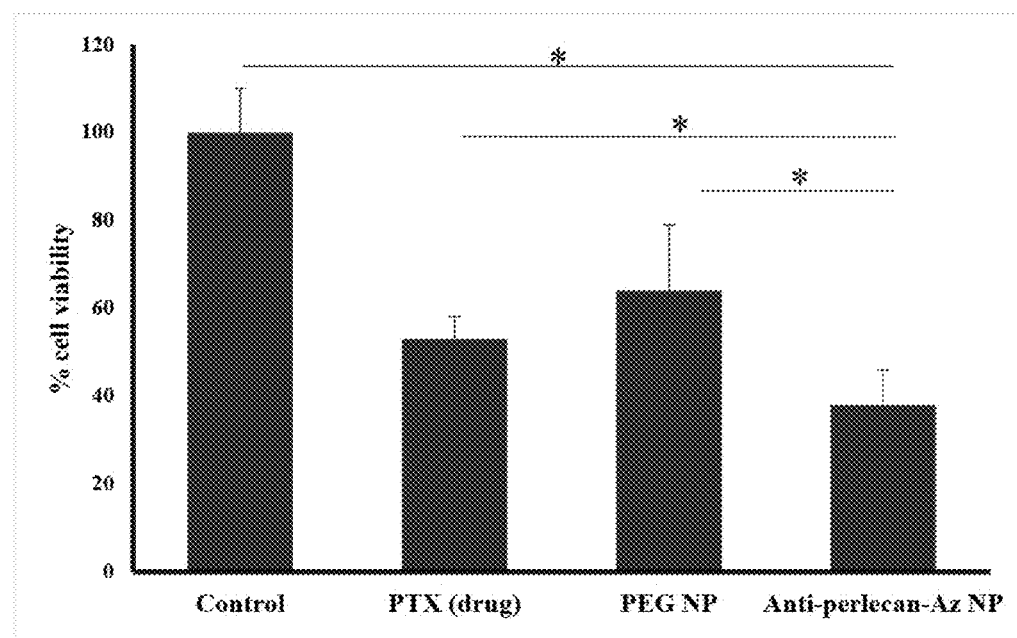

Grey = control cells

Red line – anti-perlecan-azide

Figure 26
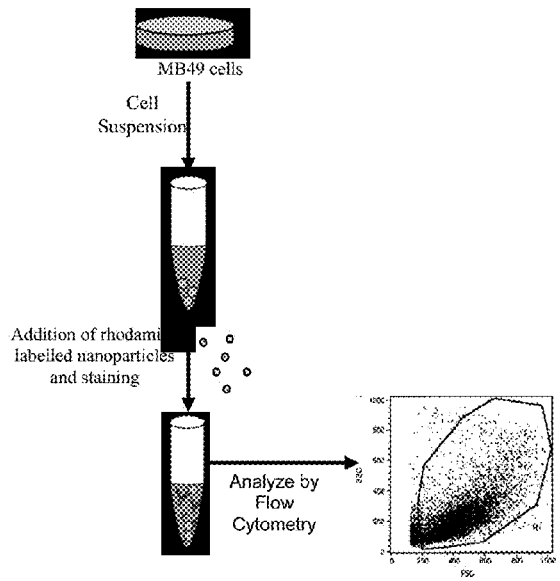
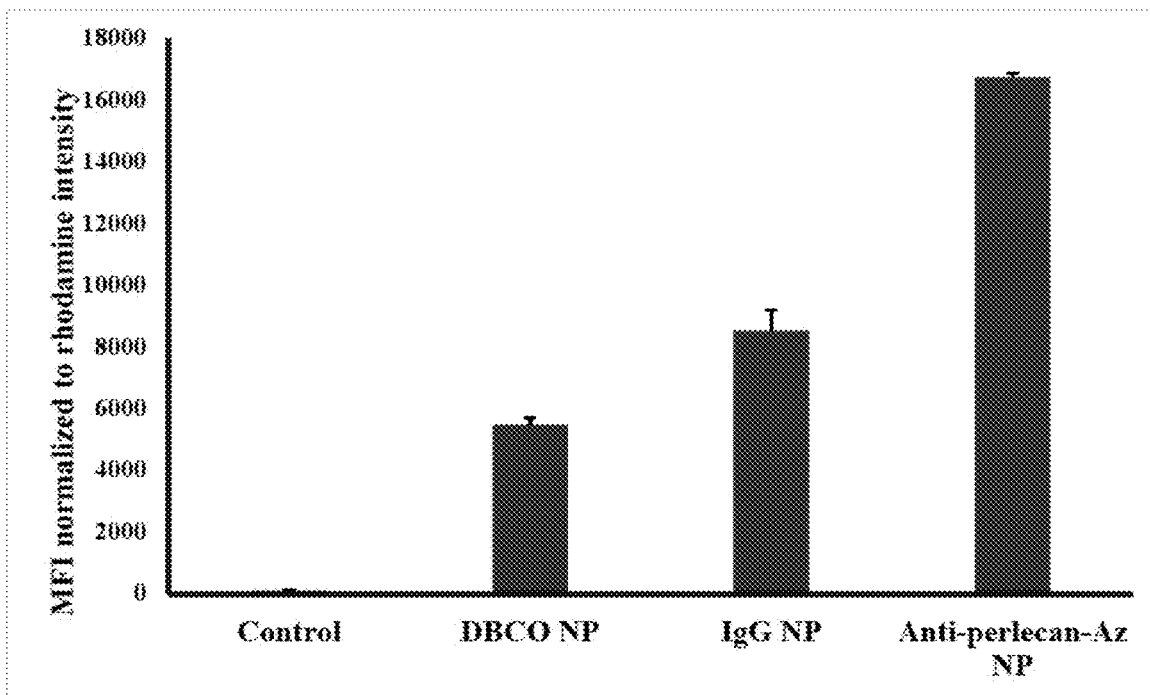

Figure 27
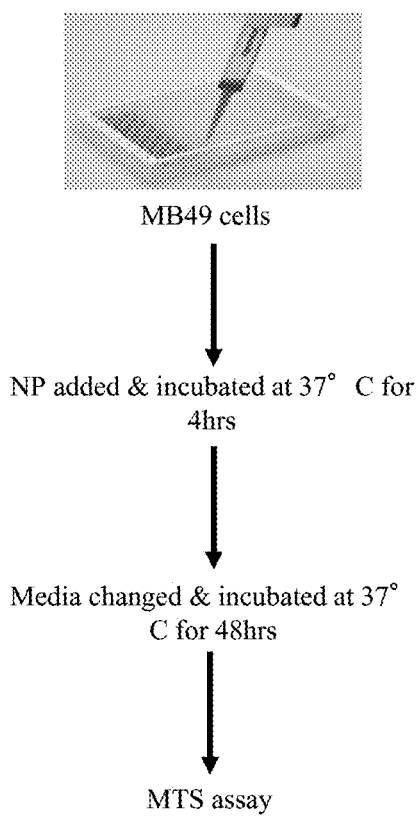
MB49 cells
↓
NP added & incubated at 37° C for 4hrs
↓
Media changed & incubated at 37° C for 48hrs
↓
MTS assay
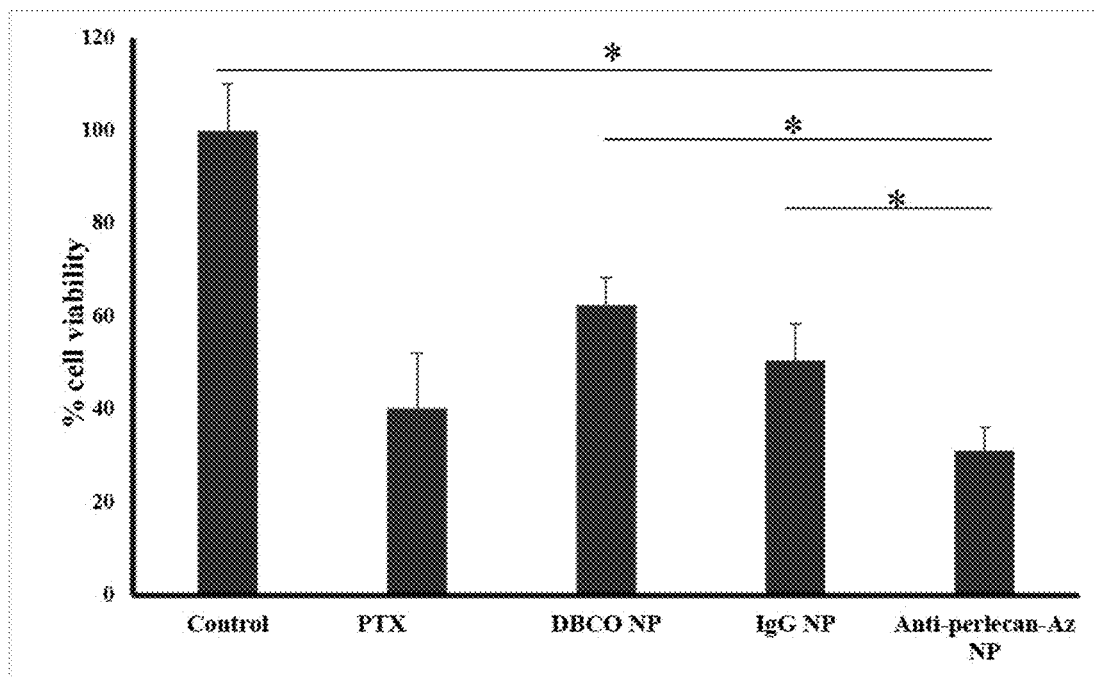

ANTIBODY FRAGMENTS FOR DETECTING CANCER AND METHODS OF USE

CROSS-REFERENCE TO RELATED APPLICATION

This application claims priority to U.S. Provisional Application No. 62/793,726, filed on Jan. 17, 2019. The entire content of the application referenced above is hereby incorporated by reference herein.

SEQUENCE LISTING

The instant application contains a Sequence Listing which has been filed electronically in ASCII format and is hereby incorporated by reference in its entirety. Said ASCII copy, created on Jun. 8, 2020, is named 09531_478US1_SL.txt and is 34,635 bytes in size.

BACKGROUND OF THE INVENTION

While increased awareness, diagnostic advances and molecularly-targeted therapies have improved breast cancer outcomes, mortality and morbidity remain high. 296,000 new diagnoses and 39,000 fatalities of breast cancer were expected in 2013 in U.S. women. Early detection and screening methods result in a favorable prognostic outlook for women diagnosed with breast cancer. In contrast, patients who present with evidence of metastatic disease have a five-year survival rate of 24% (American Cancer Society, 2014. Cancer Facts & Figures 2014. Atlanta). These statistics indicate that breast cancer can be managed with the current standard of care, when the patient presents with cancer confined to the site of origin. The dramatic reduction in survival rates upon evidence of metastasis suggests an urgent need to focus on the development of therapies/technologies designed to detect and eliminate metastatic cancer.

Accordingly, there exists the need for new reagents for the detection and treatment of cancer, in particular therapies and reagents capable of effecting therapeutic and diagnostic benefits.

SUMMARY OF THE INVENTION

The present invention provides in certain embodiments an isolated antibody or fragment thereof, comprising a heavy chain variable region and a light chain variable region, wherein the heavy chain variable region comprises heavy chain complementarity-determining regions comprising the amino acid sequences of SEQ ID NOs: 2, 3 and 4, and wherein the light chain variable region comprises light chain complementarity-determining regions comprising the amino acid sequences of SEQ ID NOs: 5, 6 and 7.

The present invention provides in certain embodiments an isolated antibody or fragment thereof, comprising at least one heavy chain variable region and at least one light chain variable region, wherein the heavy chain variable region comprises heavy chain complementarity-determining regions comprising the amino acid sequences of SEQ ID NOs:2, 3 and 4, and wherein the light chain variable region comprises light chain complementarity-determining regions comprising the amino acid sequences of SEQ ID NOs: 5, 6 and 7.

In certain embodiments, the antibody or antibody fragment is (a) an immunoglobulin (Ig) G molecule; or (b) a single-chain antibody, a Fab fragment, or a F(ab')2 fragment.

The present invention provides in certain embodiments an isolated antibody or fragment thereof that specifically binds to membrane protein HSPG2 (Perlecan), comprising at least one heavy chain variable region and at least one light chain variable region, wherein the heavy chain variable region comprises heavy chain complementarity-determining regions comprising the amino acid sequences of SEQ ID NOs:2, 3 and 4, and wherein the light chain variable region comprises light chain complementarity-determining regions comprising the amino acid sequences of SEQ ID NOs: 5, 6 and 7. In certain embodiments, the heavy chain variable region is encoded by SEQ ID NO: 8.

In certain embodiments, the light chain variable region is encoded by SEQ ID NO: 9.

In certain embodiments, the heavy chain is encoded by SEQ ID NO: 22 or SEQ ID NO: 10.

In certain embodiments, the light chain is encoded by SEQ ID NO: 21 or SEQ ID NO: 11.

In certain embodiments, the antibody fragment is scFv AM6 (SEQ ID NO: 1).

In certain embodiments, the antibody is IgG Tw1_S4_AM6 comprising two heavy chains each encoded by SEQ ID NO: 22 or SEQ ID NO: 10 and two light chains each encoded by SEQ ID NO: 21 or SEQ ID NO: 11.

In certain embodiments, the invention provides an immune reagent comprising (a) a first binding moiety comprising an antibody or antibody fragment described above, and (b) a second binding moiety comprising antibody or antibody fragment operably linked to the first antibody or antibody fragment.

In certain embodiments, the immune reagent is about 26-29 kDa.

In certain embodiments, both the first and the second binding moieties comprise the antibody or antibody fragment as described herein.

In certain embodiments, both the first and second scFv antibody fragments are scFv AM6 (SEQ ID NO: 1).

In certain embodiments, both the first and second binding moieties comprise IgG Tw1S4_AM6 comprising two heavy chains each encoded by SEQ ID NO: 22 or SEQ ID NO: 10 and two light chains each encoded by SEQ ID NO: 21 or SEQ ID NO: 11.

In certain embodiments, the first and second binding moieties are linked by means of a linker. In certain embodiments, the linker is a peptide linker. In certain embodiments, the peptide linker is 3 to 25 amino acid residues in length. In certain embodiments, the linker is between 3 and 12 amino acids in length.

In certain embodiments, the linker is a chemical linker.

In certain embodiments, the immune reagent further comprises a poly-His tail operably linked to either the first or second binding moieties.

The present invention provides in certain embodiments an immune reagent comprising a heavy chain encoded by a nucleic acid having 100% identity to SEQ ID NO:12 and a light chain encoded by a nucleic acid having 100% identity to SEQ ID NO:13. The present invention provides a nucleic acid encoding SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, or SEQ ID NO: 11, SEQ ID NO:12, SEQ ID NO:13, SEQ ID NO:22, or SEQ ID NO:21.

In certain embodiments, the nucleic acid further comprises a promoter to form an expression cassette.

The present invention provides in certain embodiments a vector comprising the expression cassette described above.

The present invention provides in certain embodiments a cell comprising the nucleic acid, expression cassette, or the vector described above.

The present invention provides in certain embodiments a conjugate comprising the immune reagent described above conjugated to a detection agent and/or a therapeutic agent. In certain embodiments, the conjugate comprising the immune reagent described above is conjugated to a detection agent. In certain embodiments, the conjugate comprising the immune reagent described above is conjugated to a therapeutic agent (e.g., a cytotoxic compound). In certain embodiments, the conjugate comprising the immune reagent described above is conjugated to a detection agent and a therapeutic agent.

In certain embodiments, the detection agent and/or therapeutic agent includes a radionuclide. In certain embodiments, the radionuclide is metallic. In certain embodiments, the radionuclide is selected from Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-64, Copper-67, Erbium-169, Europium-152, Gallium-64, Gallium-68, Gadolinium-153, Gadolinium-157 Gold-195, Gold-199, Hafnium-175, Hafnium-175-181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, and Zirconium-95.

In certain embodiments, the detection agent comprises a fluorescent group. In certain embodiments, the fluorescent group is fluorescein, tetrachlorofluorescein, hexachlorofluorescein, tetramethylrhodamine, rhodamine, cyanine-derivative dyes, Texas Red, Bodipy, and/or Alexa dye.

In certain embodiments, the therapeutic agent is a cytotoxic compound. In certain embodiments the therapeutic agent a chemotherapeutic agent. In certain embodiments, the chemotherapeutic agent is selected from all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Mechlorethamine, Mercaptopurine, Methotrexate, Mitoxantrone, Oxaliplatin, Paclitaxel, silicate prodrug of Paclitaxel, Pemetrexed, Teniposide, Tioguanine, Valrubicin, Vinblastine, Vincristine, Vindesine, Vinorelbine, and/or tyrosine kinase inhibitors. In certain embodiments, the tyrosine kinase inhibitor is Axitinib, Bosutinib, Cediranib, Dasatinib, Erlotinib, Gefitinib, Imatinib, Lapatinib, Lestaurtinib, Nilotinib, Semaxanib, Sunitinib, Vemurafinib and/or Vandetanib.

The present invention provides in certain embodiments a pharmaceutical composition comprising the immune reagent or the conjugate described above and a pharmaceutically acceptable excipient.

In certain embodiments, the composition comprises an immune agent, conjugate and/or the pharmaceutical composition described above operably linked to a carrier. In certain embodiments, the carrier is a nanoparticle or liposome. In certain embodiments, the nanoparticle is a polymeric nanoparticle, micellar system and/or nanocapsule, inorganic nanoparticle such as iron oxide nanoparticle, quantum dot or silica nanoparticle, polymer-based system such as dendrimer and/or polymer drug conjugate.

The present invention provides in certain embodiments a method for detecting cancer in an animal comprising administering a therapeutically effective amount of a conjugate described above to the animal. In certain embodiments, the cancer is melanoma, breast cancer or prostate cancer.

The present invention provides in certain embodiments a method for treating or preventing cancer in an animal comprising administering a therapeutically effective amount of an immune reagent or conjugate described above to the animal. In certain embodiments, the cancer is melanoma, breast cancer or prostate cancer. In certain embodiments, the cancer is breast cancer.

The present invention provides in certain embodiments an immune reagent or a conjugate described above for use in medical therapy.

The present invention provides in certain embodiments an immune reagent or a conjugate described above for the prophylactic or therapeutic treatment of cancer.

The present invention provides in certain embodiments the use of an immune reagent of or a conjugate described above to prepare a medicament for treating cancer in an animal.

The present invention provides in certain embodiments a method of detecting a HSPG2, comprising contacting a cell with an immune reagent or a conjugate described above.

The present invention provides in certain embodiments a method of detecting cancer cells in a test tissue sample, comprising contacting the test sample with a conjugate of as described above and measuring a signal from the detection agent, wherein a signal from the test sample that is greater than a signal from a non-cancerous control sample indicates the presence of cancer cells in the test tissue sample. In certain embodiments, signal from the test sample is 1-100% greater than the signal from the control sample.

The present invention provides in certain embodiments a method of detecting cancer in an animal (e.g., a human), comprising administering a conjugate described above to the animal and measuring a signal from the detection agent, wherein a signal greater than a signal from a control animal without cancer indicates the animal has cancer. In certain embodiments, the signal from the animal is 1-100% greater than the signal from the control animal. In certain embodiments, the signal from the detection agent is measured using PET imaging.

The present invention provides in certain embodiments a method of determining the effectiveness of a cancer therapy in an animal, comprising (a) administering a conjugate described above to the animal and measuring a first signal (e.g., a radioactive signal) from the detection agent; (b) administering a cancer therapy; (c) administering a conjugate described above to the animal and measuring a second signal (e.g., a radioactive signal) from the detection agent;

and (d) comparing the first signal with the second signal, wherein the cancer therapy is effective if the second signal is less than the first signal.

In certain embodiments, second signal is 1-100% less than the first signal.

In certain embodiments, first and second signals are measured using PET imaging.

The present invention provides in certain embodiments a kit comprising (a) an immune reagent described above; (b) instructions for conjugating a radionuclide to the immune reagent to generate a radiolabeled conjugate; and (c) instructions for administering the radiolabeled conjugate to an animal. In certain embodiments, the kit further comprises a radionuclide.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 8A-8B. The nucleic acid and amino acid sequences for Tw1S4_AM6 IgG light and heavy chains are provided.

FIG. 9. The nucleic acid and amino acid sequences for Tw1S4_6 IgG light chain is provided.

FIG. 10. The nucleic acid and amino acid sequences for Tw1S4_AM6 scFv is provided. Also provided are the nucleic acid and amino acid sequences for linkers hma (human muscle aldolase) and EASGGPE (SEQ ID NO: 24).

FIG. 14A. Biotin quantification assay: anti-CD133-Azide had 2.74 molecules of biotin per IgG. FIG. 14B. Biotin quantification assay: anti-CD133-Azide had 1.44 molecules of biotin per IgG.

FIG. 21. Cell Uptake of Antibody Conjugated Nanoparticles.

FIG. 22. In vitro efficacy of anti-perlecan conjugated NP.

FIG. 26. Cell uptake of antibody conjugated nanoparticles.

FIG. 27. In vitro cytotoxicity with antibody conjugated nanoparticles.

DETAILED DESCRIPTION OF THE INVENTION

Figures 1A, 1B, 1C, 1D:
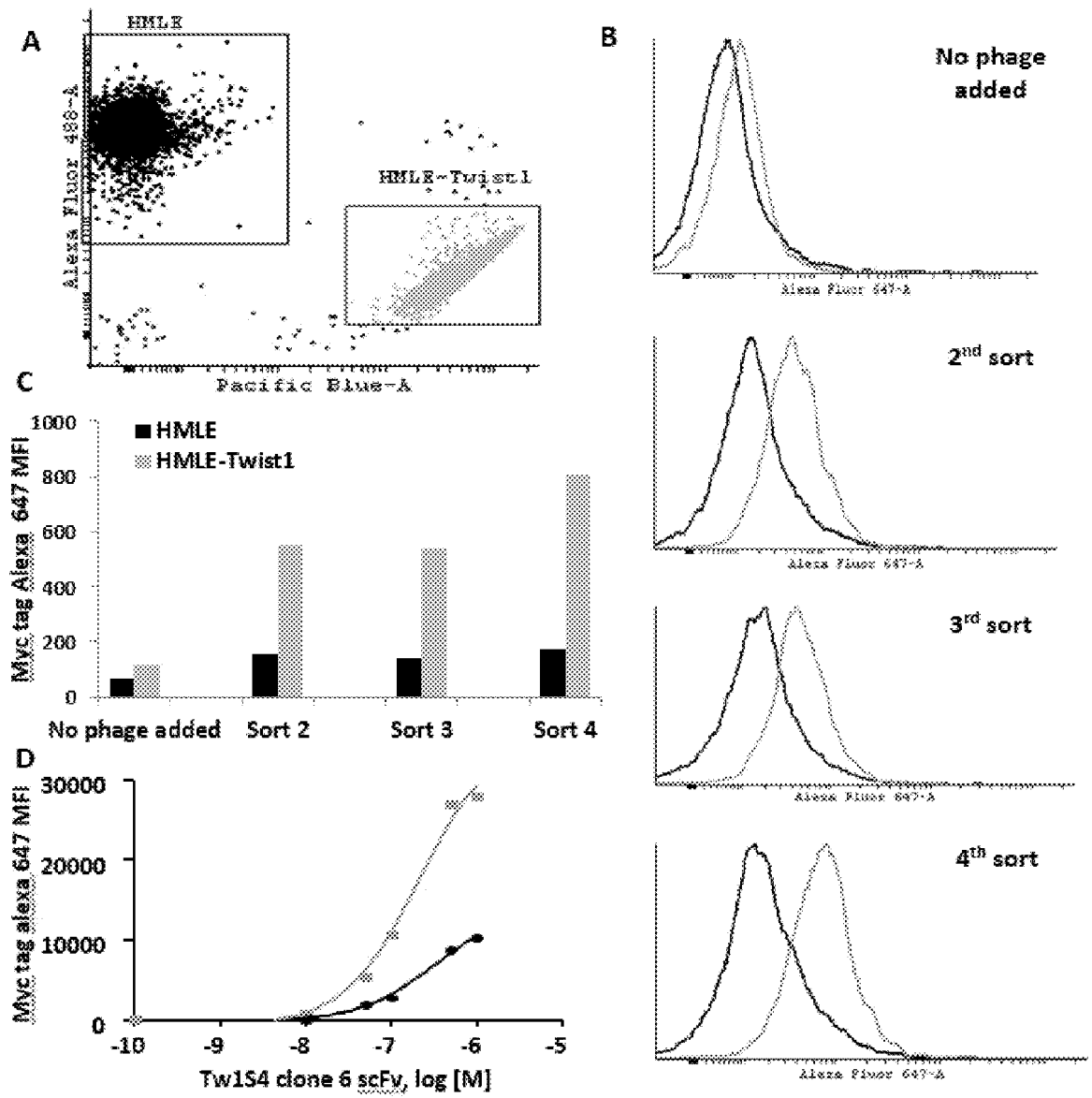
FIGS. 1A-1D. Phage display-based competitive cell panning (A) Representative dot plot of phage enrichment experiment. HMLE cells were labeled with CFSE green fluorescent viability dye while Twist1 cells were labeled with Calcein violet in separate tubes, washed, and mixed at a 1:1 ratio. $10^9$ phage from sorted sub-libraries were added to the cell mixture and incubated with agitation for 30 min at 4° C. Cells were subsequently washed and labeled with an antibody recognizing the C-Myc epitope tag of phage displaying scFv, followed by secondary Alexa-fluor 647 conjugate. (B) HMLE and Twist1 cells were discriminated based on fluorescent labeling scheme in A. Each cell population was subsequently analyzed for C-Myc-Alexa 647 fluorescence intensity to determine relative binding of polyclonal phage sub-libraries (C) Graphical depiction of data in B. (D) Clone 6 scFv was identified as selective binder to resistant HMLE-Twist1 cells (squares) relative to HMLE (circles), hereafter referred to as Tw1S4_6.

Epithelial to mesenchymal transition (EMT) in metastatic breast cancer: the idea of metastatic dissemination as a late stage event in tumor progression has been challenged recently, as emerging evidence suggests an early appearance in tumorigenesis. Conventional diagnosis of metastatic cancer entails detection of regional lymph node dissemination, yet 20-40% of lymph node negative patients are believed to harbor occult metastases in bone marrow, and other distant sites, at the time of diagnosis. Metastasis of breast carcinoma includes invasion, intravasation into circulation, survival, extravasation out of the circulation, and seeding of distant mi-crometastatic lesions. The key cellular/molecular events that give rise to metastatic dissemination in breast cancer begin as a histological transition from carcinoma in situ to invasive carcinoma. Release of cytokines, growth factors, and matrix proteases by inflammatory cells, endothelial cells, and resident fibroblasts of activated tumor stroma leads to dissolution of basement membrane that contain benign neoplastic lesions. Tumor cell interaction with the stroma then produces profound morphogenetic changes in neoplastic epithelial cells. These changes manifest as a loss of the polarized, cell-cell adhesion characteristics of epithelial cells, and acquisition of motile, invasive fibroblast-like characteristics. This process, termed EMT, plays a critical role in the generation of circulating tumor cells (CTCs) and eventual metastasis by generating invasive carcinoma cells that enter the circulation seed distant metastases.

Recent technological advances have enabled clinicians to obtain immediate evidence of metastatic dissemination via enumeration of CTCs in peripheral blood of patients. While numerous CTC detection technologies exist at various stages of pre-clinical development, CELLSEARCH is the only method currently approved by the FDA for this purpose. Using this technology, a cutoff of five CTCs per 7.5 mL blood was able to predict good vs. poor prognosis in metastatic breast cancer patients. CTC enumeration now has established prognostic value in both early stage and advanced breast cancer. Concerns have been raised, however, regarding the method of CTC capture using CELLSEARCH, which is reliant upon an antibody directed against the epithelial cell adhesion molecule (EpCAM). The critical assumption of the CELLSEARCH platform is that CTCs will express EpCAM, owing to the fact that the cell of origin in carcinoma is epithelial. However, the key cellular event that gives rise to CTCs is the acquisition of an invasive EMT phenotype within the primary tumor. This phenotypic change manifests as a loss of the polarized, cell-cell adhesion characteristics of epithelial cells, and is accompanied by increased motility and invasiveness. A number of recent studies have demonstrated EMT marker gene expression in CTCs of breast cancer patients. Importantly, studies employing CTC enumeration as a means to monitor therapeutic response have demonstrated that CTCs identified at follow-up are enriched for EMT marker gene expression. These findings suggest that the full complement of CTCs is not being effectively monitored or characterized with existing CTC technologies that rely solely on epithelial marker expression.

The CELLSEARCH system is comprised of two components in series: the CellTracks autoprep fluidics system and the CellTracks analyzer. The autoprep is an automated fluidics system for immunomagnetic enrichment of CTCs, employing ferrofluids conjugated to antibodies targeting EpCAM. The CellTracks analyzer is a semi-automated fluorescence microscopy station. Immunocytochemistry is used to characterize the captured CTCs for lymphocyte marker exclusion (CD45) and Cytokeratin expression, to confirm CTCs are of epithelial origin. The reliance on a positive selection step (EpCAM magnetic beads) to enrich for CTCs results in a sample of high purity. However, owing to the exceedingly rare occurrence of CTCs in blood, many events with low to intermediate expression, such as EMT+ CTCs, are missed.

Certain embodiments of the present invention provide a nucleic acid encoding an antibody or antibody fragment described above. In certain embodiments, the nucleic acid further comprises a promoter. Examples include, but are not limited to, a lac promoter, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In certain embodiments, other control elements, such as enhancers and the like, will be of particular use. In certain embodiments, a gIII signal sequence is included at the 5' terminus. In certain embodiments, the nucleic acid further comprises a nucleic acid encoding a c-myc tag and a nucleic acid encoding a (His)$_6$ tag (SEQ ID NO: 29) that are positioned in-frame at the 3' terminal of the bispecific antibody. The gIII signal sequence directs the polypeptide into the periplasmic space, where it can fold correctly in a soluble form. The c-myc tag is used to analyze the expression level of the bispecific scFv, and (His)$_6$ tag (SEQ ID NO: 29) can be used to purify the bispecific scFv protein.

Certain embodiments of the present invention provide an expression cassette comprising the nucleic acid sequence described above and a promoter.

Certain embodiments of the present invention provide a vector comprising the expression cassette described above. In certain embodiments, the vector is a viral vector. In certain embodiments, the viral vector is an adenoviral, lentiviral, adeno-associated viral (AAV), poliovirus, HSV, or murine Maloney-based viral vector.

Certain embodiments of the present invention provide the vector or expression cassette described above.

Certain embodiments of the present invention provide a therapeutic composition comprising a bispecific antibody described above, in combination with a physiologically-acceptable, non-toxic vehicle.

Cancer

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, head and neck cancer, and melanoma.

Antibodies and Antibody Fragments

Certain embodiments of the present invention provide an immune reagent comprising a first scFv antibody fragment that specifically binds to membrane protein HSPG2 (Perlecan). In certain embodiments, the scFv is the structure as provided in FIG. 10.

As used herein, the term "antibody" includes scFv, humanized, fully human or chimeric antibodies, single-chain antibodies, diabodies, and antigen-binding fragments of antibodies that do not contain the Fc region (e.g., Fab fragments). In certain embodiments, the antibody is a human antibody or a humanized antibody. A "humanized" antibody contains only the three CDRs (complementarity determining regions) and sometimes a few carefully selected "framework" residues (the non-CDR portions of the variable regions) from each donor antibody variable region recombinantly linked onto the corresponding frameworks and constant regions of a human antibody sequence. A "fully humanized antibody" is created in a hybridoma from mice genetically engineered to have only human-derived antibody genes or by selection from a phage-display library of human-derived antibody genes.

As used herein, the term "antibody" includes a single-chain variable fragment (scFv or "nanobody"), humanized, fully human or chimeric antibodies, full length antibodies, single-chain antibodies, diabodies, and antigen-binding fragments of antibodies (e.g., Fab fragments). Dondelinger et al., "Understanding the Significance and Implications of Antibody Numbering and Antigen-Binding Surface/Residue Definition," Frontiers in Immunology, Vol. 9, Article 2278 (18 Oct. 2018). A scFv is a fusion protein of the variable region of the heavy ($V_H$) and light chains ($V_L$) of an immunoglobulin that is connected by means of a linker. In certain embodiments, the linker between the $V_H$ and $V_L$ is a peptide. In certain embodiments, the linker is short, about 3-25 amino acids in length. In certain embodiments the linker is about 3-12 amino acids in length. If flexibility is important, the linker will contain a significant number of glycines. If solubility is important, serines or threonines will be utilized in the linker. The linker may link the amino-terminus of the $V_H$ to the carboxy-terminus of the $V_L$, or the linker may link the carboxy-terminus of the $V_H$ to the amino-terminus of the $V_L$. Divalent (also called bivalent) scFvs can be generated by linking two scFvs. For example, a divalent scFv can be made by generating a single peptide containing two $V_H$ and two $V_L$ regions. Alternatively, two peptides, each containing a single $V_H$ and a single $V_L$ region can be dimerized (also called "diabodies"). In certain embodiments, the linker that is used to link the two scFv moieties is a peptide. In certain embodiments, the linker is short, about 3-25 amino acids in length.

As used herein, the term "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are produced from hybridoma cultures not contaminated with other immunoglobulins.

The adjective "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods. The monoclonal antibodies used in the present invention can be also isolated from a phage antibody library. The monoclonal antibodies of the present invention particularly comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention.

As used herein, the term "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis, PCR-based mutagenesis, cassette mutagenesis, and the like. Such mutants comprise an amino acid sequence which is at least 70% identical to the amino acid sequence of a heavy or light chain variable region of the antibody, more preferably at least 75%, even more preferably at least 80%, still more preferably at least 85%, yet more preferably at least 90%, and most preferably at least 95% identical. As used herein, the term "sequence identity" is defined as the percentage of residues identical to those in the antibody's original amino acid sequence, determined after the sequences are aligned and gaps are appropriately introduced to maximize the sequence identity as necessary.

Specifically, the identity of one nucleotide sequence or amino acid sequence to another can be determined using the algorithm BLAST. Programs such as BLASTN and BLASTX were developed based on this algorithm. To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST)).

Monoclonal antibodies can be prepared by methods known to those skilled in the art.

In another embodiment, antibodies or antibody fragments can be isolated from an antibody phage library. There are also reports that describe the production of high affinity (nM range) human antibodies based on chain shuffling, and combinatorial infection and in vivo recombination, which are methods for constructing large-scale phage libraries. These technologies can also be used to isolate monoclonal antibodies, instead of using conventional hybridoma technology for monoclonal antibody production.

Antibodies to be used in the present invention can be purified by a method appropriately selected from known methods, such as the protein A-Sepharose method, hydroxyapatite chromatography, salting-out method with sulfate, ion exchange chromatography, and affinity chromatography, or by the combined use of the same.

The present invention may use recombinant antibodies produced by gene engineering. The genes encoding the antibodies obtained by a method described above are isolated from the hybridomas. The genes are inserted into an appropriate vector, and then introduced into a host. The present invention provides the nucleic acids encoding the antibodies of the present invention, and vectors comprising these nucleic acids. Specifically, using a reverse transcriptase, cDNAs encoding the variable regions (V regions) of the antibodies are synthesized from the mRNAs of hybridomas. After obtaining the DNAs encoding the variable regions of antibodies of interest, they are ligated with DNAs encoding desired constant regions (C regions) of the antibodies, and the resulting DNA constructs are inserted into expression vectors. Alternatively, the DNAs encoding the variable regions of the antibodies may be inserted into expression vectors comprising the DNAs of the antibody C regions. These are inserted into expression vectors so that the genes are expressed under the regulation of an expression regulatory region, for example, an enhancer and promoter. Then, host cells are transformed with the expression vectors to express the antibodies. The present invention provides cells expressing antibodies of the present invention. The cells expressing antibodies of the present invention include cells and hybridomas transformed with a gene of such an antibody.

In certain embodiments, an amino acid residue is mutated into one that allows the properties of the amino acid side-chain to be conserved. Examples of the properties of amino acid side chains comprise: hydrophobic amino acids (A, I, L, M, F, P, W, Y, V), hydrophilic amino acids (R, D, N, C, E, Q, G, H, K, S, T), and amino acids comprising the following side chains: aliphatic side-chains (G, A, V, L, I, P); hydroxyl group-containing side-chains (S, T, Y); sulfur atom-containing side-chains (C, M); carboxylic acid- and amide-containing side-chains (D, N, E, Q); base-containing side-chains (R, K, H); and aromatic-containing side-chains (H, F, Y, W). The letters within parenthesis indicate the one-letter amino acid codes. Amino acid substitutions within each group are called conservative substitutions. It is well known that a polypeptide comprising a modified amino acid sequence in which one or more amino acid residues is deleted, added, and/or substituted can retain the original biological activity. The number of mutated amino acids is not limited, but in general, the number falls within 40% of amino acids of each CDR, and preferably within 35%, and still more preferably within 30% (e.g., within 25%). The identity of amino acid sequences can be determined as described herein.

In the present invention, recombinant antibodies artificially modified to reduce heterologous antigenicity against humans can be used. Examples include chimeric antibodies and humanized antibodies. These modified antibodies can be produced using known methods. A chimeric antibody includes an antibody comprising variable and constant regions of species that are different to each other, for example, an antibody comprising the antibody heavy chain and light chain variable regions of a nonhuman mammal such as a mouse, and the antibody heavy chain and light chain constant regions of a human. Such an antibody can be obtained by (1) ligating a DNA encoding a variable region of a mouse antibody to a DNA encoding a constant region of a human antibody; (2) incorporating this into an expression vector; and (3) introducing the vector into a host for production of the antibody.

A humanized antibody, which is also called a reshaped human antibody, is obtained by substituting an H or L chain complementarity determining region (CDR) of an antibody of a nonhuman mammal such as a mouse, with the CDR of a human antibody. Conventional genetic recombination techniques for the preparation of such antibodies are known. Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see, European Patent Application No. EP 239,400, and International Patent Application No. WO 96/02576). Human antibody FRs that are ligated via the CDR are selected where the CDR forms a favorable antigen-binding site. The humanized antibody may comprise additional amino acid residue(s) that are not included in the CDRs introduced into the recipient antibody, nor in the framework sequences. Such amino acid residues are usually introduced to more accurately optimize the antibody's ability to recognize and bind to an antigen. For example, as necessary, amino acids in the framework region of an antibody variable region may be substituted such that the CDR of a reshaped human antibody forms an appropriate antigen-binding site.

The isotypes of the antibodies of the present invention are not limited. The isotypes include, for example, IgG (IgG1, IgG2, IgG3, and IgG4), IgM, IgA (IgA1 and IgA2), IgD, and IgE. The antibodies of the present invention may also be antibody fragments comprising a portion responsible for antigen binding, or a modified fragment thereof. The term "antibody fragment" refers to a portion of a full-length antibody, and generally to a fragment comprising an antigen-binding domain or a variable region. Such antibody fragments include, for example, Fab, F(ab')2, Fv, single-chain Fv (scFv) which comprises a heavy chain Fv and a light chain Fv coupled together with an appropriate linker, diabody (diabodies), linear antibodies, and multispecific antibodies prepared from antibody fragments. Previously, antibody fragments were produced by digesting natural antibodies with a protease; currently, methods for expressing them as recombinant antibodies using genetic engineering techniques are also known.

An "Fv" fragment is the smallest antibody fragment, and contains a complete antigen recognition site and a binding site. This region is a dimer dimer) wherein the variable regions of each of the heavy chain and light chain are strongly connected by a noncovalent bond. The three CDRs of each of the variable regions interact with each other to form an antigen-binding site on the surface of the $V_H$-$V_L$ dimer. In other words, a total of six CDRs from the heavy and light chains function together as an antibody's antigen-binding site. However, a variable region (or a half Fv, which contains only three antigen-specific CDRS) alone is also known to be able to recognize and bind to an antigen, although its affinity is lower than the affinity of the entire binding site. Thus, a preferred antibody fragment of the present invention is an Fv fragment, but is not limited thereto. Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody. A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody," even when it is not identical to an antibody fragment produced by protease digestion. Fab'-SH is Fab' with one or more cysteine residues having free thiol groups in its constant region. An F(ab') fragment is produced by cleaving the disulfide bond between the cysteine residues in the hinge region of $F(ab')_2$. Other chemically crosslinked antibody fragments are also known to those skilled in the art. Pepsin digestion of an antibody yields two fragments; one is a F(ab')2 fragment which comprises two antigen-binding domains and can cross-react with antigens, and the other is the remaining fragment (referred to as pFc'). Herein, an antibody fragment equivalent to that obtained by pepsin digestion is referred to as a "$F(ab')_2$-like antibody" when it comprises two antigen-binding domains and can cross-react with antigens. Such antibody fragments can also be produced, for example, by genetic engineering. Such antibody fragments can also be isolated, for example, from the antibody phage library described above. Alternatively, $F(ab')_2$-SH fragments can be recovered directly from hosts, such as *E. coli*, and then allowed to form $F(ab')_2$ fragments by chemical crosslinking. In an alternative method, $F(ab')_2$ fragments can be isolated directly from a culture of recombinant hosts.

The term "diabody (Db)" refers to a bivalent antibody fragment constructed by gene fusion. In general, a diabody is a dimer of two polypeptide chains. In the each of the polypeptide chains, a light chain variable region ($V_L$) and a heavy chain variable region ($V_H$) in an identical chain are connected via a short linker, for example, a linker of about five residues, so that they cannot bind together. Because the linker between the two is too short, the $V_L$ and $V_H$ in the same polypeptide chain cannot form a single chain V region fragment, but instead form a dimer. Thus, a diabody has two antigen-binding domains. When the $V_L$ and $V_H$ regions against the two types of antigens (a and b) are combined to form $V_{La}$-$V_{Hb}$ and $V_{Lb}$-$V_{Ha}$ via a linker of about five residues, and then co-expressed, they are secreted as bispecific Dbs. The antibodies of the present invention may be such Dbs.

A single-chain antibody (also referred to as "scFv") can be prepared by linking a heavy chain V region and a light chain V region of an antibody. Methods for preparing single-chain antibodies are known in the art. In such scFvs, the heavy chain V region and the light chain V region are linked together via a linker, preferably, a polypeptide linker). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain or the V region of the heavy chain of the above antibody, and a DNA encoding the light chain or the V region of the light chain of the above antibody; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" in the present invention also encompasses the above-described antibodies.

The antibodies obtained can be purified to homogeneity. The antibodies can be isolated and purified by a method routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectrofocusing, for example. Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F. F. (Pharmacia). Antibodies can also be purified by utilizing antigen binding, using carriers on which antigens have been immobilized.

The antibodies of the present invention can be formulated according to standard methods (see, for example, Remington's Pharmaceutical Science, latest edition, Mark Publishing Company, Easton, U.S.A.), and may comprise pharmaceutically acceptable carriers and/or additives. The present invention relates to compositions (including reagents and pharmaceuticals) comprising the antibodies of the invention, and pharmaceutically acceptable carriers and/or additives. Exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, and other adjuvants, including, for example, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

If necessary, antibodies of the present invention may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules). Moreover, methods for making sustained-release drugs are known, and these can be applied for the antibodies of the present invention.

Nucleic Acid Molecules Encoding Antibodies

The present invention further provides nucleic acid sequences that encode the antibodies described above.

The term "nucleic acid" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a fraction of a given nucleic acid molecule. Deoxyribonucleic acid (DNA) in the majority of organisms is the genetic material while ribonucleic acid (RNA) is involved in the transfer of information contained within DNA into proteins. The term "nucleotide sequence" refers to a polymer of DNA or RNA that can be single- or double-stranded, optionally containing synthetic, non-natural or altered nucleotide bases capable of incorporation into DNA or RNA polymers. The terms "nucleic acid," "nucleic acid molecule," "nucleic acid fragment," "nucleic acid sequence or segment," or "polynucleotide" may also be used interchangeably with gene, cDNA, DNA and RNA encoded by a gene.

The terms "protein," "peptide" and "polypeptide" are used interchangeably herein.

The invention encompasses isolated or substantially purified nucleic acid or protein compositions. In the context of the present invention, an "isolated" or "purified" DNA molecule or an "isolated" or "purified" polypeptide is a DNA molecule or polypeptide that exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis that encode the native protein, as well as those that encode a polypeptide having amino acid substitutions. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance, the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid which encodes a polypeptide is implicit in each described sequence.

"Recombinant DNA molecule" is a combination of DNA sequences that are joined together using recombinant DNA technology and procedures used to join together DNA sequences.

The terms "heterologous DNA sequence," "exogenous DNA segment" or "heterologous nucleic acid," each refer to a sequence that originates from a source foreign to the particular host cell or, if from the same source, is modified from its original form. Thus, a heterologous gene in a host cell includes a gene that is endogenous to the particular host cell but has been modified. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" DNA sequence is a DNA sequence that is naturally associated with a host cell into which it is introduced.

"Wild-type" refers to the normal gene, or organism found in nature without any known mutation.

"Genome" refers to the complete genetic material of an organism.

A "vector" is defined to include, inter alia, any plasmid, cosmid, phage or binary vector in double or single stranded linear or circular form which may or may not be self-transmissible or mobilizable, and which can transform prokaryotic or eukaryotic host either by integration into the cellular genome or exist extrachromosomally (e.g., autonomous replicating plasmid with an origin of replication).

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. The expression of the nucleotide sequence in the expression cassette may be under the control of a constitutive promoter or of an inducible promoter that initiates transcription only when the host cell is exposed to some particular external stimulus. In the case of a multicellular organism, the promoter can also be specific to a particular tissue or organ or stage of development.

Such expression cassettes will comprise the transcriptional initiation region of the invention linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

The term "RNA transcript" refers to the product resulting from RNA polymerase catalyzed transcription of a DNA sequence. When the RNA transcript is a perfect complimentary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, inducible promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation in a cell of an endogenous gene, transgene, as well as the transcription and stable accumulation of sense (mRNA) or functional RNA. In the case of antisense constructs, expression may refer to the transcription of the antisense DNA only. Expression may also refer to the production of protein.

"Transcription stop fragment" refers to nucleotide sequences that contain one or more regulatory signals, such as polyadenylation signal sequences, capable of terminating transcription. Examples of transcription stop fragments are known to the art.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule.

The terms "trans-acting sequence" and "trans-acting element" refer to DNA or RNA sequences whose function does not require them to be on the same molecule.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information (available on the world wide web at ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See the world wide web at ncbi.nlm.nih.gov. Alignment may also be performed manually by visual inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, or 79%, at least 80%, 81%, 82%, 83%, 84%, 85%, 86%, 87%, 88%, or 89%, at least 90%, 91%, 92%, 93%, or 94%, and at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, and at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to the reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point ($T_m$) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. Conservative substitutions, such as exchanging one amino acid with another having similar properties, are preferred.

Thus, the genes and nucleotide sequences of the invention include both the naturally occurring sequences as well as mutant forms. Likewise, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms".

"Transformed," "transgenic," and "recombinant" refer to a host cell or organism into which a heterologous nucleic acid molecule has been introduced. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

A "transgenic" organism is an organism having one or more cells that contain an expression vector.

By "portion" or "fragment," as it relates to a nucleic acid molecule, sequence or segment of the invention, when it is linked to other sequences for expression, is meant a sequence having at least 80 nucleotides, more preferably at least 150 nucleotides, and still more preferably at least 400 nucleotides.

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

Linkers

In certain embodiments, the antibody is linked to a detection agent (e.g., fluorophore) by means of a linker.

In certain embodiments, an aliphatic or ethylene glycol linker (as are well known to those will skill in the art) is used. In certain embodiments, the linker is a phosphodiester linkage. In certain embodiments, the linker is a phosphorothioate linkage. In certain embodiments, other modified linkages between the modifier groups like dyes and quencher and the bases are used in order to make these linkages more stable, thereby limiting degradation to the nucleases.

In certain embodiments, the linker is a binding pair. In certain embodiments, the "binding pair" refers to two molecules which interact with each other through any of a variety of molecular forces including, for example, ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-avidin, hormone-receptor, receptor-ligand, enzyme-substrate, IgG-protein A, antigen-antibody, and the like. In certain embodiments, a first member of the binding pair comprises avidin or streptavidin and a second member of the binding pair comprises biotin.

In certain embodiments, the antibody is linked to the detection agent by means of a covalent bond.

In certain embodiments, the antibody probe, i.e., an antibody that is operably linked to a detection agent, is also operably linked to a solid substrate. For example, the antibody probe may be linked to a magnetic bead.

Chemistries that can be used to link the detection agent to the antibody are known in the art, such as disulfide linkages, amino linkages, covalent linkages, etc. In certain embodiments, aliphatic or ethylene glycol linkers that are well known to those with skill in the art can be used.

Figure 11:
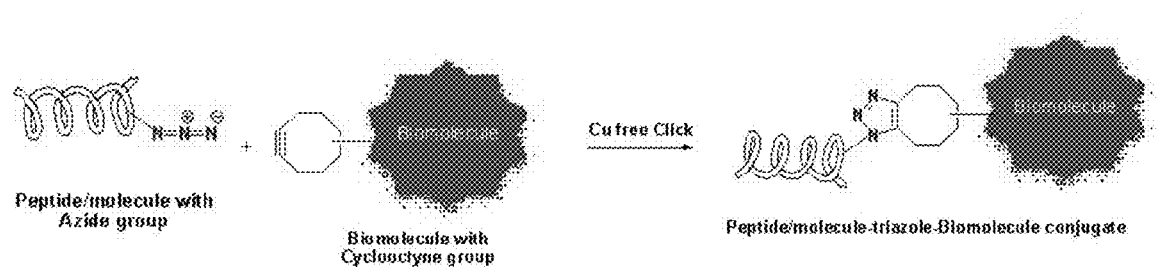
FIG. 11. Strain-Promoted Alkyne-Azide Cycloaddition (SPAAC). The reactive group is an azide.
Figure 12:
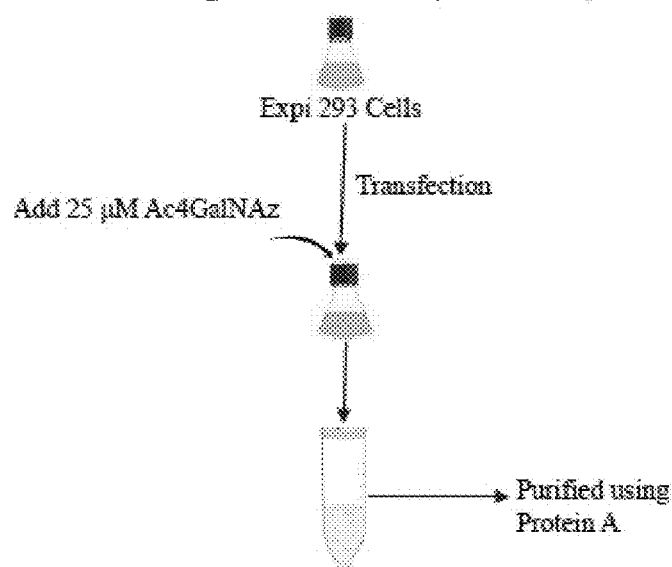
FIG. 12. Anti-perlecan-Az (Am6-Az).
Figure 13:
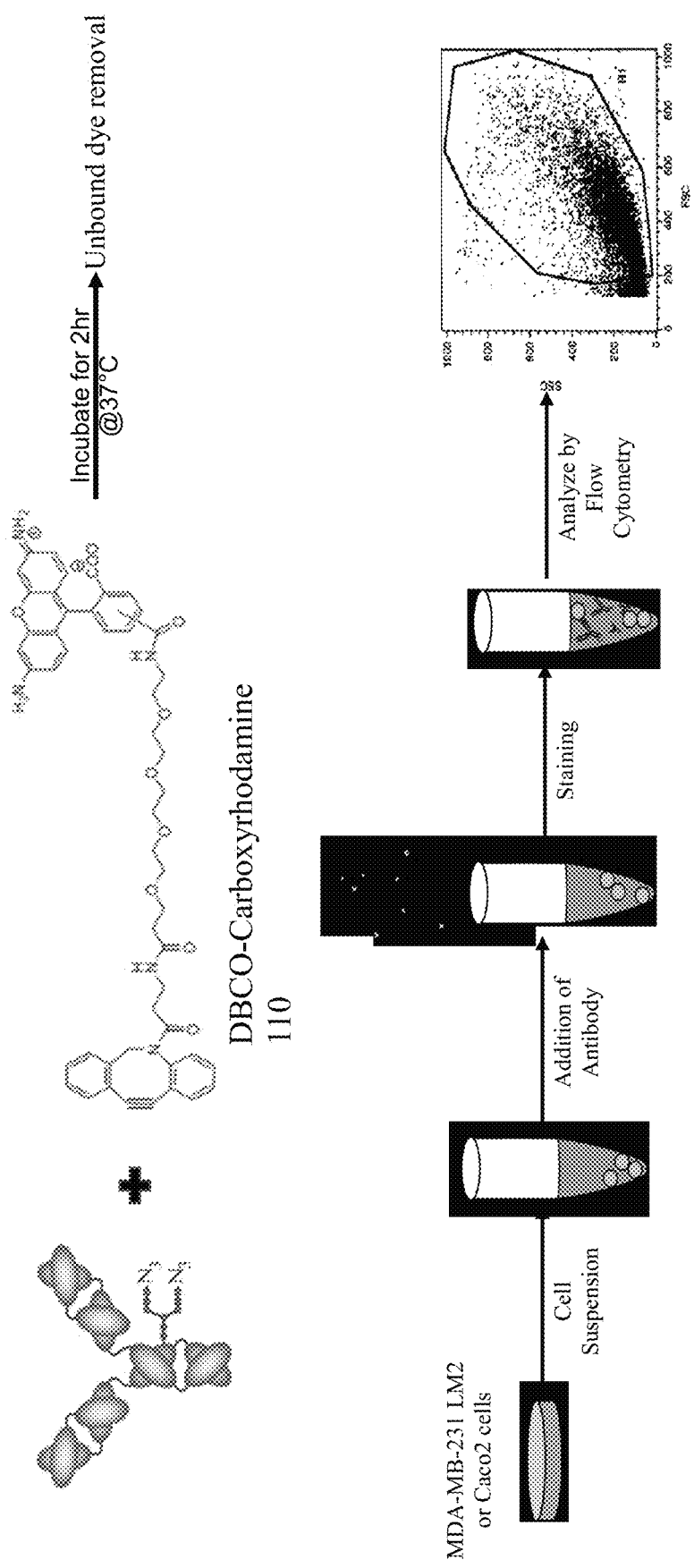
FIG. 13. Presence of azide on antibody.
Figure 14A:
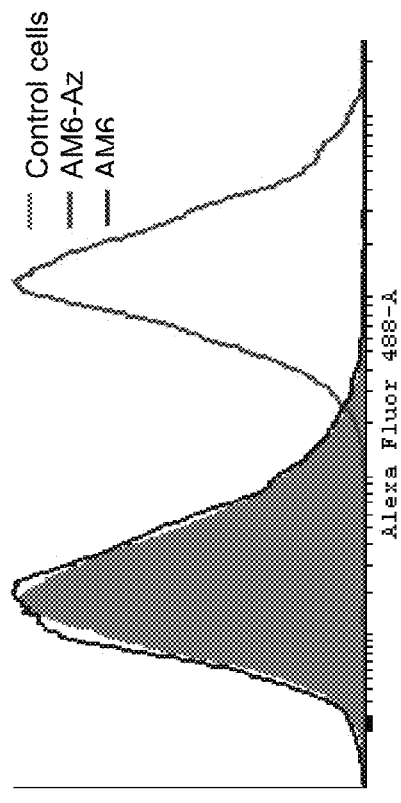
FIGS. 14A-14B. Glycoengineered antibody shows presence of azide.
Figure 14B:
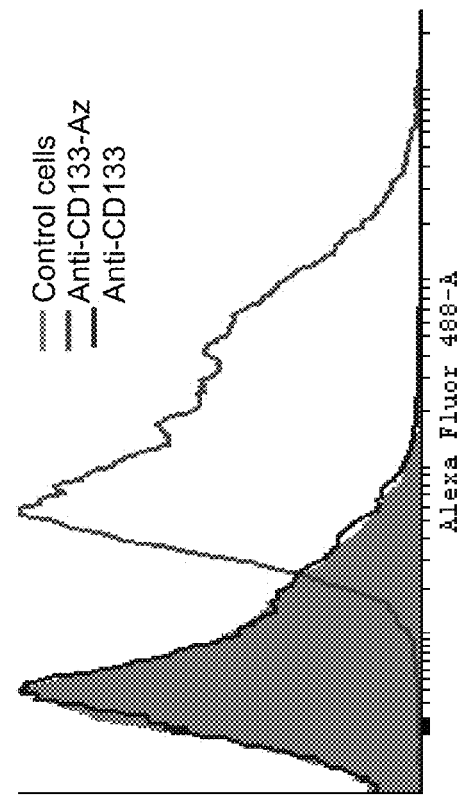
Figure 15:
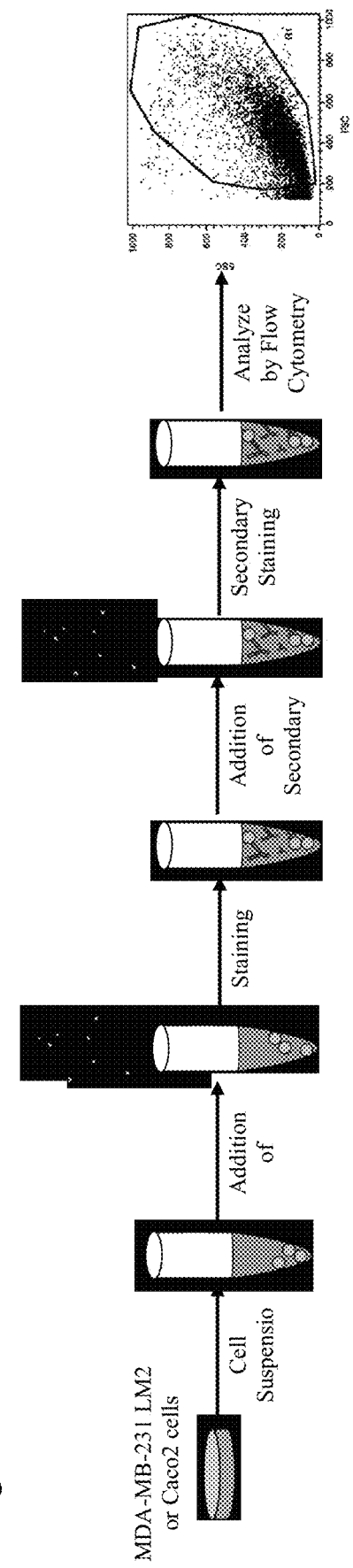
FIG. 15. Binding affinity to target antigen.

In certain embodiments, the antibody can be glycoengineered, such as with an azide group. Strain-Promoted Alkyne-Azide Cycloaddition (SPAAC) can then be utilized to covalently conjugate a biomolecule to the antibody (FIG. 11).

Detection and Therapeutic Compositions

In certain embodiments, the immune reagents described above can be prepared as pharmaceutically-acceptable compositions. In certain embodiments, the immune reagents are administered so as to result in the detection of a cancer. In certain embodiments, the immune reagents are administered so as to result in the treatment of a cancer. The amount administered will vary depending on various factors including, but not limited to, the composition chosen, the particular disease, the weight, the physical condition, and the age of the mammal. Such factors can be readily determined by the clinician employing animal models or other test systems, which are well known to the art.

In certain embodiments, the antibody is conjugated to a therapeutic compound, such as a cytotoxic compound. Methods of conjugating antibodies to compounds are known in the art. In certain embodiments, the therapeutic compound is conjugated to the diabody by means of a maleimide-thiol linkage through cysteines on the immune reagent.

In certain embodiments, the immune reagent is operably linked to one or more chemotherapeutic agent. In certain embodiments, the chemotherapeutic agent is selected from all-trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Mechlorethamine, Mercaptopurine, Methotrexate, Mitoxantrone, Oxaliplatin, Paclitaxel, silicate prodrug of Paclitaxel, Pemetrexed, Teniposide, Tioguanine, Valrubicin, Vinblastine, Vincristine, Vindesine, Vinorelbine, and/or tyrosine kinase inhibitors. In certain embodiments, the tyrosine kinase inhibitor can include Axitinib, Bosutinib, Cediranib, Dasatinib, Erlotinib, Gefitinib, Imatinib, Lapatinib, Lestaurtinib, Nilotinib, Semaxanib, Sunitinib, Vemurafinib and/or Vandetanib.

In certain embodiments, the immune reagent is operably linked to a nanoparticle. In certain embodiments, the nanoparticle is a polymeric nanoparticle, micellar system and/or nanocapsule, inorganic nanoparticle such as iron oxide nanoparticle, quantum dot or silica nanoparticle, polymer-based system such as dendrimer and/or polymer drug conjugate.

Treatment, Detection and Diagnostic Methods

Certain embodiments of the invention provide a pharmaceutical composition comprising an immune reagent, antibody or antibody fragment and a pharmaceutically acceptable excipient.

Certain embodiments of the invention provide a method for treating or preventing cancer in an animal (e.g., a human) comprising administering a therapeutically effective amount of an immune reagent, antibody or antibody fragment to the animal.

The terms "treat" and "treatment" refer to both therapeutic treatment and prophylactic or preventative measures, wherein the object is to prevent or slow down (lessen) an undesired physiological change or disorder, such as the growth, development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The invention also provides an antibody specific for HSPG2 (Perlecan) for use in medical therapy.

The invention also provides an antibody specific for HSPG2 (Perlecan) for the prophylactic or therapeutic treatment of cancer.

The invention also provides the use of an antibody specific for HSPG2 (Perlecan) to prepare a medicament for treating cancer in an animal (e.g. a mammal such as a human).

In certain embodiments, the cancer is melanoma, breast cancer or prostate cancer.

In certain embodiments, the cancer is breast cancer.

Certain embodiments of the invention provide a method of detecting a HSPG2 (Perlecan) molecule, comprising contacting a cell with an immune reagent, antibody or antibody fragment specific for HSPG2. Certain embodiments of the invention provide a method of detecting a circulating tumor cell comprising contacting a cell with an immune reagent, antibody or antibody fragment specific for HSPG2. In certain embodiments, the detection agent comprises a chelating group labeled with a radionuclide. In certain embodiments, the detection agent comprises a fluorescent group. In certain embodiments, the method further comprises quantifying the concentration of HSPG2 on the surface of the cell by measuring a signal from the detection agent (e.g., a fluorescent signal or a radioactive signal).

Certain embodiments of the invention provide a method of detecting cancer cells in a test tissue sample, comprising contacting the test sample with an antibody specific for HSPG2 and measuring a signal from the detection agent (e.g., a radioactive signal or fluorescent signal), wherein a signal greater than a signal from a non-cancerous control sample indicates the presence of cancer cells in the test tissue sample. In certain embodiments, the signal from the test sample is 1-100% greater than the signal from the control sample. In certain embodiments, the signal from the test sample is 10%, 20%, 30%, 40%, 50%, 60%, 70%, 80%, or 90% greater than the signal from the control sample.

Certain embodiments of the invention provide an in vivo method of detecting cancer in an animal (e.g., a human patient), comprising administering an antibody specific for HSPG2 to the animal and measuring a signal (e.g., a radioactive signal or fluorescent signal emitting in the near infrared range) from the detection agent, wherein a signal greater than a signal from a control animal without cancer indicates the animal has cancer. Certain embodiments of the invention provide a method of detecting a circulating tumor cell comprising contacting a cell with an immune reagent, antibody or antibody fragment specific for HSPG2. In certain embodiments, the signal from the animal is 1-100% greater than the signal from the control animal. In certain embodiments, the signal from the animal is 10%, 20%, 30%, 40%, 50%, 60%, 70%, 80%, or 90% greater than the signal from the control animal. In certain embodiments of the invention, the signal from the detection agent is measured using PET imaging or Mill.

Certain embodiments of the invention provide a method for determining the effectiveness of a cancer therapy in an animal (e.g., a human patient), comprising (1) administering an antibody specific for HSPG2 to the animal and measuring a first signal (e.g., a radioactive signal or fluorescent signal emitting in the near infrared range) from the detection agent; (2) administering a cancer therapy; (3) administering an antibody specific for HSPG2 to the animal and measuring a second signal (e.g., a radioactive signal or fluorescent signal emitting in the near infrared range) from the detection agent; and (4) comparing the first signal with the second signal, wherein the cancer therapy is effective if the second signal is less than the first signal.

In certain embodiments, the second signal is 1-100% less than the first signal. In certain embodiments, the first signal is 10%, 20%, 30%, 40%, 50%, 60%, 70%, 80%, or 90% less than the first signal. In certain embodiments of the invention, the signal from the detection agent is measured using PET imaging or by MM. In certain embodiments of the invention, the signal from the detection agent is measured using PET imaging.

Certain embodiments of the invention provide a kit comprising: (1) an antibody specific for HSPG2; and (2) instructions for administering the antibody to an animal.

Certain embodiments of the invention provide a kit comprising: (1) an antibody specific for HSPG2; (2) instructions for conjugating a radionuclide to the antibody to generate a radiolabeled conjugate; and (3) instructions for administering the radiolabeled conjugate to an animal.

Certain embodiments of the invention provide a kit comprising: (1) an antibody specific for HSPG2; (2) a radionuclide; (3) instructions for conjugating the radionuclide to the antibody to generate a radiolabeled conjugate; and (4) instructions for administering the radiolabeled conjugate to an animal.

Administration

The antibody specific for HSPG2 can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present antibodies may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the conjugates may be combined with one or more excipients and used in the form of ingestible tablets, buccal tablets, troches, capsules, elixirs, suspensions, syrups, wafers, and the like. Such compositions and preparations should contain at least 0.1% of conjugates. The percentage of the compositions and preparations may, of course, be varied and may conveniently be between about 2 to about 60% of the weight of a given unit dosage form. The amount of the conjugates in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the conjugates, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the conjugates may be incorporated into sustained-release preparations and devices.

The conjugates may also be administered intravenously or intraperitoneally by infusion or injection. Solutions of the conjugates can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

In certain embodiments, an antibody specific for HSPG2 is operably linked to a detection agent, wherein the detection agent comprises a chelating group labeled with a radionuclide, is formulated for administration by infusion.

The pharmaceutical dosage forms suitable for injection or infusion can include sterile aqueous solutions or dispersions or sterile powders comprising the conjugates which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the conjugates in the required amount in the appropriate solvent with various the other ingredients enumerated above, as required, followed by filter sterilization. In the case of sterile powders for the preparation of sterile injectable solutions, the preferred methods of preparation are vacuum drying and the freeze drying techniques, which yield a powder of the conjugates plus any additional desired ingredient present in the previously sterile-filtered solutions.

For topical administration, the present conjugates may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present conjugates can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the antibody specific for HSPG2 can be determined by comparing their in vitro activity, and in vivo activity in animal models. Methods for the extrapolation of effective dosages in mice, and other animals, to humans are known to the art; for example, see U.S. Pat. No. 4,938,949.

The amount of the conjugates, or derivative thereof, required for use in treatment will vary with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Conjugates of the invention can also be administered in combination with other therapeutic agents, for example, other agents that are useful for the treating cancer. Examples of such agents include chemotherapeutic agents. Accordingly, one embodiment the invention also provides a composition comprising an antibody specific for HSPG2, at least one other therapeutic agent, and a pharmaceutically acceptable diluent or carrier. The invention also provides a kit comprising an antibody specific for HSPG2, at least one other therapeutic agent, packaging material, and instructions for administering an antibody specific for HSPG2 and the other therapeutic agent or agents to an animal to treat cancer.

The invention will now be illustrated by the following non-limiting Examples.

Example 1

Discovery of HSPG2 (Perlecan) as a Therapeutic Target in Triple Negative Breast Cancer Abstract Epithelial-to-mesenchymal transition (EMT) plays an important role in disease progression in triple negative breast cancer (TNBC). Using a phage display-based whole cell biopanning procedure, we developed and affinity-matured a fully human antibody that binds to tumor cells with EMT phenotype. Our studies further identified domain 1 of HSPG2 (perlecan) protein as the cognate cell surface antigen epitope bound by the antibody.

Immunohistochemistry studies utilizing patient tissue samples revealed significant cell surface expression of HSPG2 in both primary tumors and metastatic lesions compared to its expression in the extracellular matrix of normal tissues. Further, higher HSPG2 expression correlated with poor survival in TNBC. The affinity-matured antibody inhibited the growth of triple negative MDA-MB-231 tumors to a greater extent in nude mice than in NSG mice, pointing to the potential role of natural killer cell-mediated antibody-dependent cell cytotoxicity. This mechanism of action was confirmed through in vitro assays using mouse spleenocytes and human peripheral blood mononuclear cells (PBMCs). These results thus suggest HSPG2 is a promising target in metastatic TNBC and HSPG2-targeted antibodies could represent a potentially novel class of targeted therapeutics for TNBC.

Introduction

The key events that give rise to metastatic dissemination in many solid tumors involve the loss of polarized, cell-cell adhesion characteristics of epithelial cells and the acquisition of motile, invasive fibroblast-like characteristics. This process, termed epithelial to mesenchymal transition (EMT), plays a critical role in disease progression. While significant advances have been made in understanding the biology of EMT and the proteins involved, therapies that specifically target this key process are generally lacking. Further, currently available markers of EMT are either intracellular or are not specific for cancer cells and thus are not optimal for therapeutic applications.

Phage display is an effective method for generating highly target-specific antibody or peptide fragments. This method utilizes large, diverse libraries of bacteriophage displaying antibody fragments on their surface for in vitro high-throughput screening of antibody fragments against the desired peptide/antigen. Sequential enrichment of antibody fragments that display specificity for the given target eventually leads to a manageable number of candidates that can be tested for specificity. In the present experiments, we utilized a whole cell, competition-based panning procedure employing a single chain variable fragment (scFv) phage display library to identify candidate scFv fragments capable of selective binding to an EMT phenotypic cell population in triple negative breast cancer (TNBC). This biopanning procedure allows presentation of antigens in their native, physiological context thus extending its relevance to translational applications.

An isogenic cell line pair, consisting of human mammary epithelial cells and Twist-induced derivative mesenchymal-phenotypic cells, was used to screen for antibodies specific to the mesenchymal phenotype. The isogenic nature of the cell line pair provided stringent selection of markers relevant to the induction of EMT. A candidate scFv demonstrating selective binding to EMT cells was identified, affinity matured and subsequently reformatted to human IgG. Our studies further identified heparan sulfate proteoglycan 2 (HSPG2) as the cognate cell surface antigen bound by the antibody. HSPG2, also known as perlecan, is a heavily glycosylated protein component of the extra-cellular matrix (ECM) that has been shown to play a role in tethering and presentation of growth factors to receptors. However, HSPG2 expression in TNBC and, more importantly, its use as a therapeutic target have not been explored before. We investigated the expression of HSPG2 in human TNBC and its correlation with survival. We also examined the ability of anti-HSPG2 antibodies identified through phage display to specifically target and inhibit tumor growth in mouse xenograft models. Our results suggest that HSPG2 can be used as a target in metastatic TNBC.

Methods

Cell Culture Conditions

HMLE isogenic cell lines were a generous gift from the lab of Dr. Robert Weinberg. HMLE cells and HMLE-Twist1 cells were cultured in MEGM media (Lonza). MDA-MB-231-LM2 cells were obtained from Dr. Joan Massague of the Howard Hughes Medical Institute, Memorial Sloan Kettering Cancer Center (New York, N.Y., USA). Cells were cultured in MEM supplemented with 10% FBS and antibiotics.

Expression and Purification of HSPG2 Domain 1 and 5

HSPG2 domain 1 construct was previously reported. DNA sequence encoding the first 247 amino acids of human HSPG2 was cloned into pcDNA 3.3+ vector bearing a C terminal His tag. The plasmid was used to express domain 1 in suspension HEK cells. The protein was purified using HisPur Ni-NTA Chromatography Cartridges (Thermo Scientific, Illinois, USA). HSPG2 domain 5 was purchased (Santa Cruz Biotechnology).

Immunofluorescence Microscopy

Cells were plated onto 8-well CC2 chamber slides (Lab Tek) and allowed to adhere prior to fixation with 3% formaldehyde for 10 minutes. Cells were subsequently permeabilized with 0.5% v/v Triton-X 100. Following a 1-hour blocking step in 5% w/v BSA in PBS, cells were stained with dye conjugate antibodies for 1 hour in blocking buffer. Antibodies used in fluorescence microscopy experiments were: PE anti-human E-cadherin (clone 67A4, Biolegend), PE anti-human EpCAM (clone 1B7, Biolegend), Efluor 660 anti-human vimentin (clone V9, eBioscience), Biotinylated anti-human perlecan antibody (clone A7L6, Neomarkers) and streptavidin dylight 488 (Biolegend), or streptavidin APC depending on the other fluorophores in the antibody panel. All the antibodies were used at 1:250 dilution. Following staining, cells were mounted in ProLong Gold anti-fade mounting medium (Life technologies) and imaged within 24 hours. Image acquisition was performed on an Olympus Fluoview FV1000 BX2 upright confocal microscope.

ELISA

HSPG2 domains 1 and 5 were coated onto ELISA plates for 2 hours at room temperature, using a concentration of 10 µg/mL. Following three PBS washes, plates were blocked with blocking buffer (PBS, 2% BSA) for 2 hours at room temperature. Tw1S4_6 IgG diluted in blocking buffer at the indicated concentrations was plated in triplicate and incubated overnight at 4° C. The plates were then washed and incubated with 1:20,000 Protein-L HRP (Genscript) for 2 hours at room temperature. Three washes in PBS followed by incubation with TMB substrate (Sigma) for 15 minutes were performed. The peroxide solution was quenched with stop solution (Sigma), and signal intensity was quantified on a UV/Vis 96-well plate reader by measuring absorbance at 450 nm. Log concentration—response plots were generated in GraphPad Prism software. Nonlinear regression analysis was employed to generate fitted curves to the data.

Binding of Antibodies to Circulating Tumor Cells

All experiments involving animals were performed in compliance with institutional guidelines and regulations. MDA-MB-231-LM2 cells were dissociated from tissue culture plate with trypsin-EDTA, centrifuged, and washed twice with PBS. Cells were resuspended in PBS such that 50 µL contained $10^6$ cells. Cell suspensions were diluted with an equal volume of matrigel (BD Bioscience). The cell suspension was grafted subcutaneously to the right flank corresponding to mammary fat pad #9. When tumors reached 500 $mm^3$, mice were euthanized, and peripheral blood was collected by cardiac puncture. Blood samples were pooled (n=3) and PBMCs were purified using Ficoll-Paque density gradient media (GE Healthcare). Residual RBCs were lysed with BD Pharm lyse (BD bioscience). Cells were washed three times in PBS. Antibodies were diluted in flow buffer (PBS, 0.5% BSA, 2 mM EDTA) to 100 nM concentration, and cells were incubated on a rotating platform for 1 hour at 4° C. The antibodies used were VU-1D9 EpCAM Pacific Blue, Dylight647 labeled Tw1S4_6 IgG generated using a commercial labeling kit (ThermoFisher) and anti-murine CD45 PE (Biolegend, CA). Cells were sorted based on fluorescent profile on a BD FACSAria 2 cell sorting equipment. The sorted cells were collected and analyzed by immunofluorescence microscopy as described above.

Tissue Microarray Immunohistochemistry

Human tissue microarrays (Catalog Numbers T088b, MET961) were purchased from USBiomax (Rockville, Md.). Tw1S4_6 antibody was used for evaluation of perlecan expression. Standard immunohistochemistry was performed by the Comparative Pathology Shared Resource at the University of Minnesota. Images were captured on an inverted Axiovert 40 CFL microscope at 10× or 40× magnification. Quantification of HSPG2 staining was done using ImageJ software (NIH).

Flow Cytometry-Based Determination of Antibody Binding

Cells were trypsinized and aliquoted to $10^5$ cells in PBS (200 Cells were incubated with a range of antibody concentrations for 60 minutes at 4° C. on a rotating shaker. Flow cytometry buffer used was PBS, 0.5% w/v BSA, 2 mM EDTA. Following two wash steps, a goat anti-human Dylight 647 conjugate antibody was used to determine the extent of antibody binding to cells. A BD LSR2 was used to analyze cells for fluorescence. For estimation of equilibrium dissociation constants of Tw1S4_6 and Tw1S4_AM6 IgGs, binding titration curves designed to encompass the estimated $K_D$ values were performed using a BD LSR2 digital cytometer. Non-linear regression analysis was performed using the geometric MFIs from antibody binding titrations, using GraphPad Prism software. The 50% value from regression analysis is presented as the apparent $K_D$. This procedure was used for all cell lines tested for Tw1S4_6 or Tw1S4_AM6 binding.

Biolayer Inferometry-Based Determination of Antibody Binding Kinetics

We used biolayer inferometry (BLItz, Fortebio) to determine antibody binding kinetics specifically with purified HSPG2 domain 1. Ni-NTA biosensors were hydrated for 10 minutes in phosphate buffered saline. Following hydration, a 30 second baseline was established, followed by a 10-minute loading of the biosensor with 10 µg/mL HSPG2 domain 1 protein. The biosensor was then placed in PBS to establish baseline for 30 seconds. A two-step antibody association—dissociation cycle of 5 minutes each was then used to determine the kinetic association ($k_a$) and dissociation ($k_d$) rate constants. The equilibrium dissociation constant ($K_D$) was calculated as $K_D=k_d/k_a$.

Tumor Growth Inhibition Studies

MDA-MB-231-LM2 tumors were grafted in Balb/c homozygous nude mice (Charles River Labs or Jackson Labs) or Balb/c NSG mice as described above. Once tumor volumes reached 100 mm³, three doses (5 mg/kg) of the antibodies were administered through tail vein injection once every 96 hrs. Isotype human IgG and saline were used as controls (n=7 for nude mice, and n=4-6 for NSG mice). Tumor volumes were measured every third day with an electronic caliper. Tumor volumes were calculated from the ellipsoid sphere equation $V=(L^2*W)/2$, L being the longer measurement. Two Way ANOVA, with multiple comparison post-tests, was used to determine the statistical significance of the data.

Kinetics of Antibody Tumor Accumulation

Mice bearing MDA-MB-231-LM2 tumors (~300 mm³) were injected with 100 μg of labeled isotype IgG Control, Tw1S4_6 or Tw1S4_AM6. Antibodies were labeled with Cy 7 maleimide (Click Chemistry Tools, Arizona) using immunothiolation to introduce reactive thiols onto the antibody. Mice were imaged using the IVIS Spectrum In Vivo Imaging System (University of Minnesota Imaging Centre) at various time intervals over 120 hours using an excitation/emission filter of 750/775 nm. Data was acquired and analyzed using living image software. Statistical data was obtained using Two Way ANOVA, with multiple comparison post-tests.

ADCC Assays with Human PBMCs and Mouse Splenocytes

Human PBMCs (effector cells) from healthy donors were purified using Ficoll-Paque density gradient media (GE Healthcare), incubated overnight at 37° C. in RPMI (10% FBS, 1% P/S) and used for the assay the next day. Target cells (MDA-MB-231-LM2) were labeled with 8 μM CFSE (Biolegend, CA, USA) for 20 minutes at room temperature, followed by two washes. CFSE labeled target cells were then incubated with 100 nM of the relevant antibodies in suspension at 4° C. for 1 hour, washed once and then used for the assay. Effector and target cells were incubated together in 96 well plates, at the specified ratios overnight at 37° C. The next day, plates were centrifuged at 1200 RPM for 5 minutes and 50 μL of supernatant was collected and cell cytotoxicity was measured using LDH assay kit (Thermo Fisher Scientific, CA, USA). The remaining media was aspirated, followed by addition of 100 μL PBS. The plates were read using a plate reader at Ex/Em 485/528 nm to determine relative cell viability.

Mouse splenocytes were obtained from the spleen of Balb/c homozygous nude mice. The cells were stimulated for 48 hours with 500 units/mL IL2 (R&D Systems, MN, USA), after which they were washed, counted and used for ADCC assay as described above.

Human PBMCs Degranulation Assay

Human PBMCs (5×10⁵/well) were seeded in a 24-well cell culture plate. To achieve sub-optimal activation of PBMCs, polyinosinic-polycytidylic acid (poly I:C) (10 μg/ml) was added to the media. After 18 hr incubation, MDA-MB-231-LM2 cells (2.5×10⁵/well) were added to the PBMCs. Subsequently, isotype IgG control, Tw1S4_6 or Tw1S4_AM6 antibodies (200 nM) were added to the media and anti-CD107a antibody was added directly into the media. After 1 hr, brefeldin A solution (Biolegend) was added to the media. Cells were collected after 3 hr and stained with anti-CD3 and anti-CD56 antibodies. Intracellular staining of interferon gamma (IFN-γ) and granzyme B were conducted according to the manufacturer's protocol (Foxp3/Transcription Factor Staining Buffer Kit, Tonbo Bioscience). Stained cells were analyzed by flow cytometry (LSRFortessa H0081, BD bioscience).

Results

Development of EMT Phenotype Selective Tw1S4 ScFv and IgG

The Tomlinson scFv phage display library was used to pan against an isogenic mammary epithelial cell line pair (HMLE and HMLE-Twist1). Following incubation with the phage library, HMLE-Twist1 cells were flow-sorted from the mixed population, and bound phage particles were eluted for sub-library generation (FIG. 1A). A mixing ratio of 100:1 HMLE:Twist1 provided a selective pressure for deriving binders that are selective to Twist1 cells via creation of a cell surface antigen sink provided by excess HMLE cells. A clear distinction in relative binding of sub-libraries to HMLE-Twist1 cells is discernable by the second sub-library (FIG. 1B). This distinction increased to ~8-fold selective binding in the fourth sub-library (FIG. 1C). A monoclonal candidate scFv (designated Tw1S4_6) was isolated from the fourth sorted sub-library, which demonstrated selective binding to Twist1 relative to HMLE cells (FIG. 1D). Reformatting of Tw1S4_6 scFv to human IgG1 was accomplished via PCR amplification of VH and VL and subsequent sub-cloning of the variable domains into pFuse2ss vectors.

Tw1S4 IgG binds to HSPG2/Perlecan Domain 1

To elucidate the target cell surface antigen bound by Tw1S4_6, HMLE-Twist1 cell lysates were passed over immobilized Tw1S4_6. Acrylamide gel resolution of heat denatured scFv-antigen complex revealed a single, high molecular weight antigen co-eluting with Tw1S4_6 scFv.

Figures 2A, 2B, 2C, 2D, 2E, 2F, 2G:
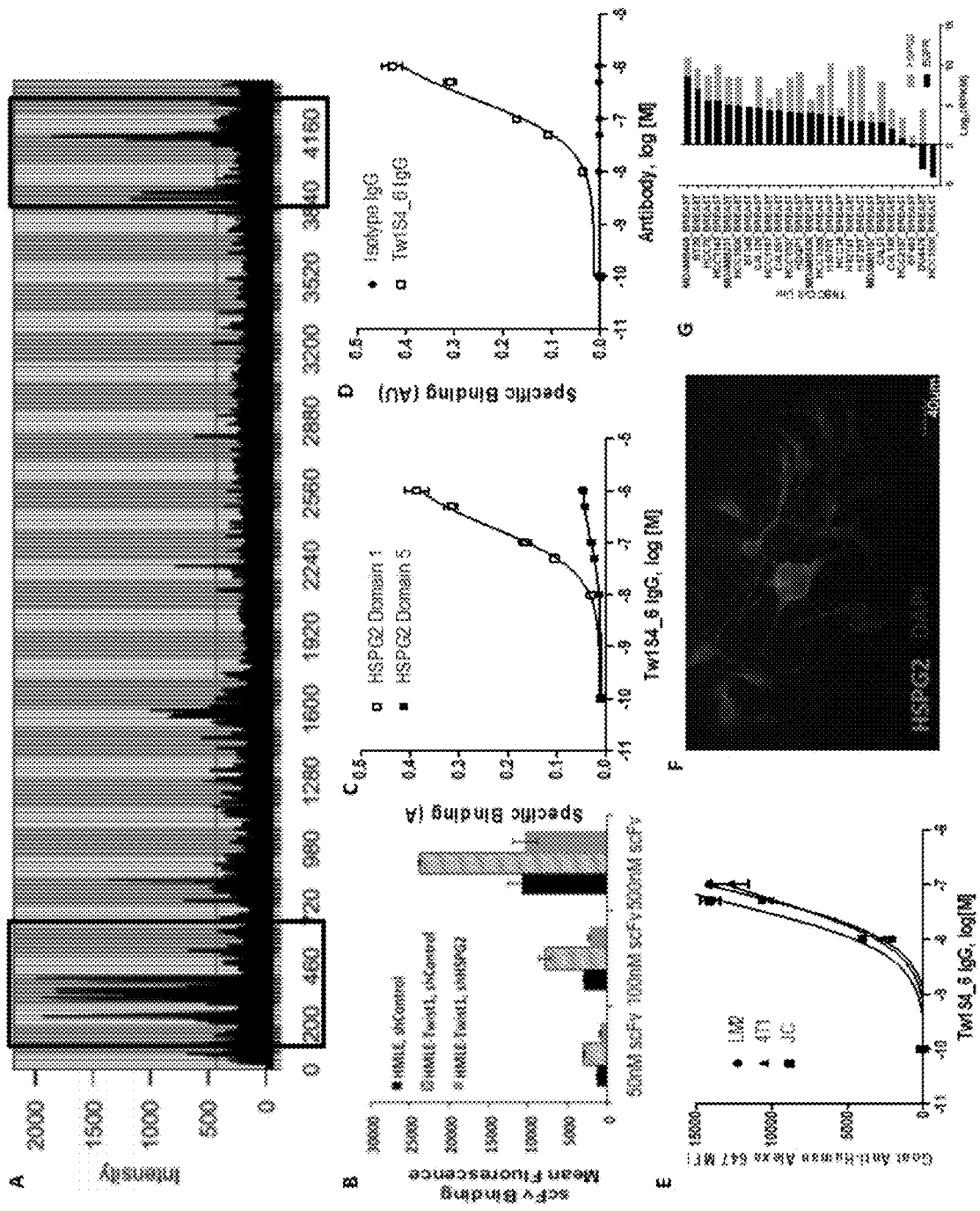
FIGS. 2A-2G. Target deconvolution and Tw1S4_6 IgG reformatting, characterization. (A) Linear epitope mapping. The epitope mapping used linear HSPG2 amino acid sequence. Tw1S4_6 binding site was identified in a high-throughput ELISA format. (B) Assessment of the relative binding of Tw1S4_6 scFv to HMLE-Twist1 cells after HSPG2 knockdown. (C) ELISA demonstrating Tw1S4_6 IgG selectively binds HSPG2 domain 1, relative to domain 5. (D) Confirmation of Tw1S4_6 selective binding to HSPG2D1 is retained in IgG format. (E) Binding titration curves for Tw1S4_6 IgG to metastatic breast cancer cell lines MDA-MB-231-LM2, 4T1, JC. (F) Immunofluorescence microscopy of MDA-MB-231-LM2 cells with commercial HSPG2 antibody A7L6. Scale bar=40 μM. (G) mRNA expression of HSPG2 and EGFR in TNBC cell lines (Broad Institute Cancel Cell Line Encyclopedia)

Tryptic digestion of the excised antigen band followed by MS/MS based peptide identification identified two separate peptides that corresponded to sequences within HSPG2. Lentiviral particles expressing shHSPG2 (or shControl) were used to knockdown HSPG2 in HMLE-Twist. HSPG2 knockdown resulted in reduced binding of Tw1S4_6 scFv and the binding affinity to HMLE-Twist-shHSPG2 was similar to that of HMLE, confirming the binding partner for Tw1S4_6 scFv was HSPG2 (FIG. 2B). Linear epitope mapping was employed to further elucidate the binding region of Tw1S4_6. Several pockets of concentrated binding were observed at N-terminal residues <500, and C-terminal residues >3800 (FIG. 2A). These regions contain the first and fifth domains of HSPG2, respectively, and are sites known to contain high molecular weight heparan sulfate modifications. Based on these results, we chose to focus further on Tw1S4_6 binding within the first and fifth domains of HSPG2. Recombinant HSPG2 domain 1 (HSPG2D1) was expressed and purified, with HSPG2D5 being available commercially. An indirect ELISA demonstrated specific binding of Tw1S4_6 to HSPG2D1 over HSPG2D5 (FIG. 2C). A similar ELISA experiment comparing Tw1S4_6 IgG with Isotype IgG binding to HSPG2D1 demonstrated specific binding of Tw1S4_6 to HSPG2D1 (FIG. 2D).

HSPG2 is Expressed In Vitro in Human Metastatic Cell Lines

Our initial extension to relevant in vitro models of cancer focused on cell lines bearing predisposition to invasion and metastasis. Binding titration curves for Tw1S4_6 were generated for three metastatic cell lines: breast to lung metastatic MDA-MB-231-LM2 (human), 4T1 (mouse) and JC (mouse). (FIG. 2E). LM2 is an MDA-MB-231 derivative of ex vivo expanded spontaneous lung metastases. A flow cytometry-based experiment with MDA-MB-231-LM2 cells was used to confirm that the target epitope on these cells was indeed HSPG2 domain 1. Increasing concentrations of free HSPG2D1, but not HSPG2D5, was able compete off Tw1S4_6 IgG binding to the cells. HSPG2 expression in MDA-MB-231-LM2 cells was confirmed via immunofluorescence microscopy using a commercially available HSPG2 antibody A7L6 (FIG. 2F). We also investigated HSPG2 and EGFR gene expression in several TNBC cell lines using the Broad Institute's Cancel Cell Line Encyclopedia (www.portals.broadinstitute.org/ccle) and found significant HSPG2 expression in 22 out 25 cell lines (FIG. 2G). In most cases, HSPG2 expression was significantly higher than EGFR, a commonly investigated therapeutic target for TNBC.

Tw1S4_6 IgG Binds to EpCAM—Sub-Set of CTCs

Figures 3A, 3B:
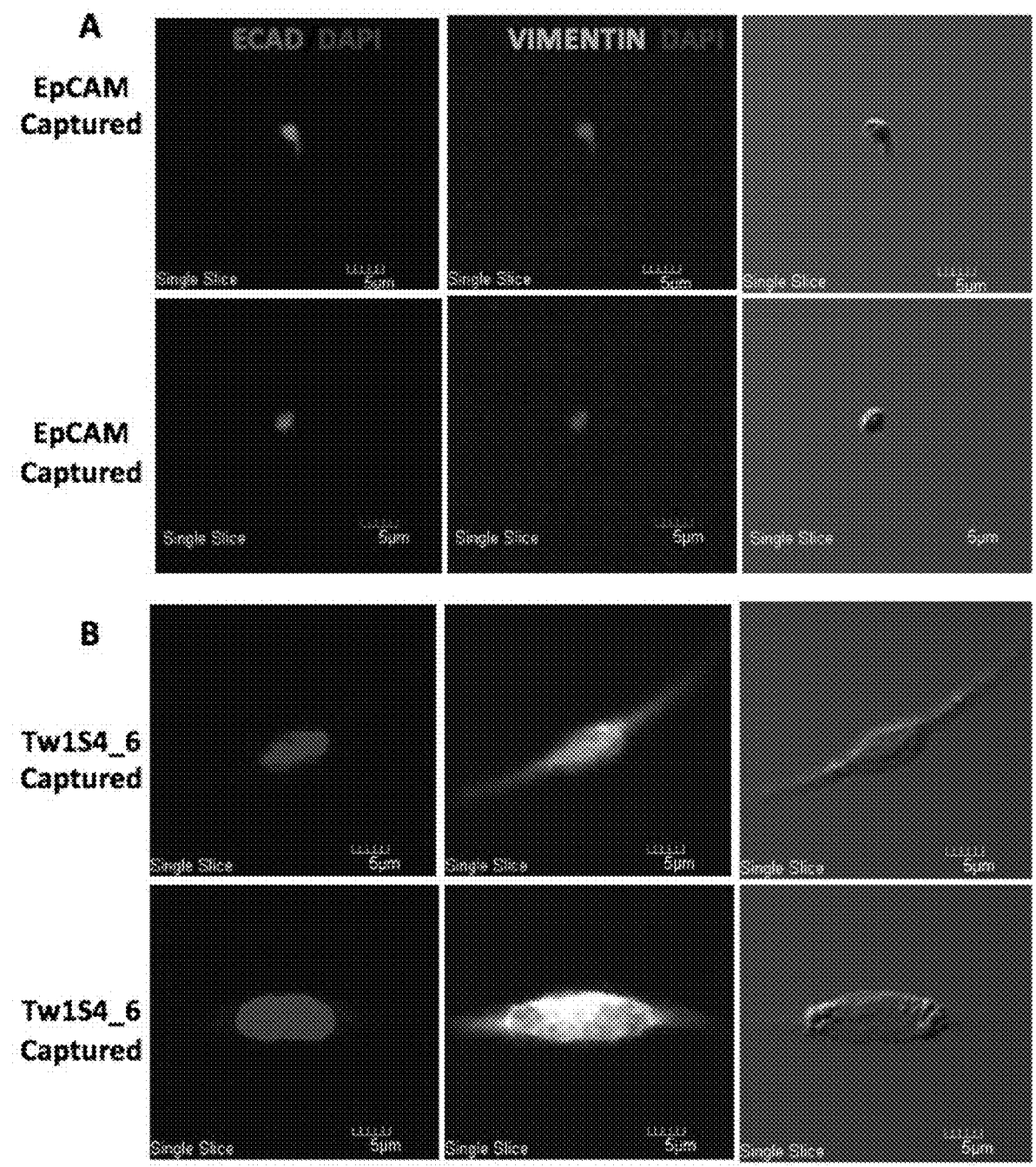
FIGS. 3A-3B. Immunofluorescence staining of sorted circulating tumor cells from MDA-MB-231-LM2 tumors. Cells captured by EpCAM IgG (A) or Tw1S4_6 IgG (B) were assayed for co-expression of EpCAM and HSPG2 using commercial antibodies. Nuclear counterstaining was performed with DAPI. Images were acquired on an Olympus FluoView FV1000 upright confocal microscope under 40× oil immersion objective.

We then evaluated the ability of Tw1S4_6 to identify EMT phenotypic CTCs in the MDA-MB-231-LM2 model. Within PBMCs from tumor bearing mice, there was a greater abundance of Tw1S4_6 positive CTCs relative to EpCAM positive CTCs (98 vs. 7). To confirm the phenotype of these two populations, sorted CTCs based on EpCAM-capture or HSPG2-capture were plated under adherent conditions, followed by immunofluorescence microscopy. EpCAM sorted cells were positive for EpCAM and negative for HSPG2. Tw1S4_6 captured CTCs displayed no EpCAM expression but were positive for HSPG2 as expected. Interestingly, EpCAM captured CTCs were positive for E-cadherin and negative for vimentin (FIG. 3A), suggesting an epithelial phenotype. In contrast, Tw1S4_6 captured CTCs were negative for E-cadherin and positive for vimentin (FIG. 3B), pointing to a mesenchymal phenotype.

HSPG2 is Expressed in Human Primary and Metastatic Tumors

Figures 4A, 4B, 4C, 4D, 4E, 4F, 4G, 4H:
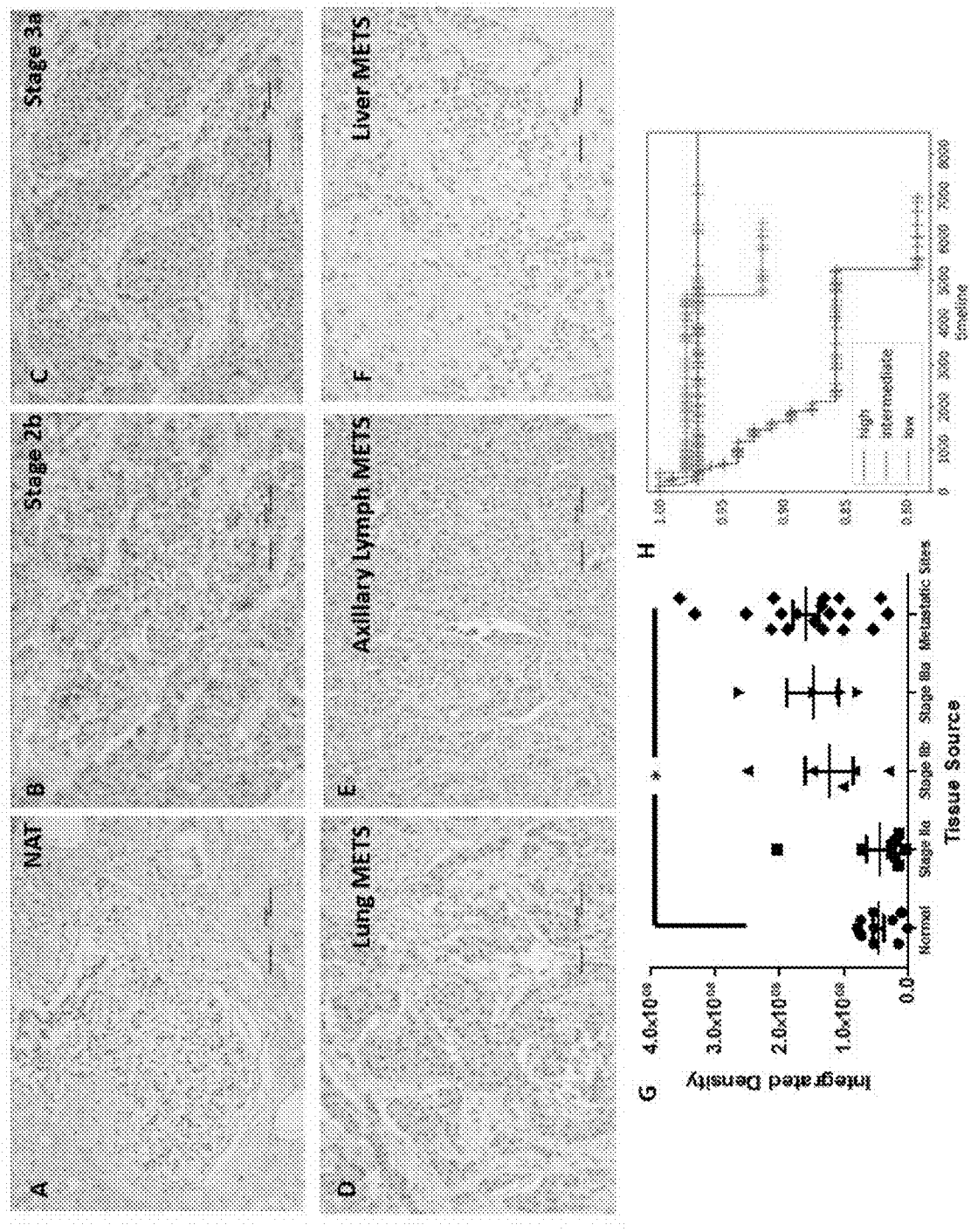
FIGS. 4A-4H. Immunohistochemistry for HSPG2 expression on human tissue microarrays. (A-F) Tw1S4_6 IgG was used to stain a breast cancer tissue microarray. The staining pattern of HSPG2 changes from interstitial to predominantly cellular with advancing stage. (G) HSPG2 expression is observed at increasing intensity with advancing tumor stages, the highest being tumor metastatic sites (*P<0.05; one-way ANOVA with Kruskal Wallis post-test) (H) Survival Analysis based on HSPG2 Expression. All patient and HSPG2 expression data was obtained from METABRIC. For patients with TNBC, high HSPG2 expression correlates with significantly poorer survival (P<0.01, multi-group log-rank test).

We next examined HSPG2 expression in human tumors. Interestingly, normal adjacent breast tissue was lightly stained in the extracellular matrix compartment (FIG. 4A), whereas stage 2 and 3 tissues revealed a strong staining of malignant intraductal epithelium (FIGS. 4B, 4C) and within cells invading the surrounding stroma (FIG. 4C). Lack of staining in the same tissue panel with an isotype human IgG confirmed that Tw1S4_6 staining was due to a specific binding event. Importantly, intense staining of malignant cells was observed in breast cancer-derived liver, lung and lymphatic metastases (FIGS. 4D-4F), pointing to the continued expression of HSPG2 in metastatic cancer cells. Quantification of staining revealed a clear correlation between tumor stage and HSPG2 expression. HSPG2 expression increased with advancing tumor stages, with the highest expression being observed at metastatic sites (P=0.0001, One-way ANOVA, Kruskal Wallis post-test).

Higher Expression of HSPG2 Correlates with Poor Patient Survival

To determine the association between HSPG2 expression and breast cancer survival, we conducted a survival analysis using 2,433 breast cancer patients from METABRIC database. In the case of all breast cancer subtypes, differential expression of HSPG2 had no correlation with patient survival (P>0.05). When the pre-stratified analysis was narrowed to patients with TNBC, we observed a significant decrease in survival with higher HSPG2 expression in TNBC (P<0.05). A univariate cox regression to assess the overall association between HSPG2 expression and patient survival revealed a hazard ratio of 7.945, indicating that higher HSPG2 expression is associated with a significantly poorer survival (P<0.01). Higher HSPG2 expression was still associated with significantly poorer survival after adjusting the known breast cancer prognostic factors such as age, stage and grade.

Affinity Maturation of Tw1S4_6 Antibody

While Tw1S4_6 IgG demonstrated good selectivity for EMT phenotypic tumor cells, its low affinity ($K_D$~125-275 nM) was a limitation. Thus, prior to evaluating its therapeutic potential, the binding affinity of Tw1S4_6 was improved. The affinity maturation approach was reliant upon mutagenesis of key residues within complementarity determining regions (CDRs) of Tw1S4_6 scFv. This approach is meant to simulate the process of somatic hypermutation that occurs in the latter stages of B-cell maturation in vivo. A whole cell based FACS sorting procedure was used to select for scFv displaying increased binding to MDA-MB-231-LM2 cells from the affinity-matured library. Following the cell sorting procedure, screening of candidate clones led to the identification of AM6 scFv (SEQ ID NO: 1), which was subsequently formatted to IgG termed Tw1S4_AM6. The nucleic acid and amino acid sequences for the Tw1S4_AM6 IgG heavy and light chains are provided in FIGS. 8A-8B. The nucleic acid and amino acid sequences for the parent Tw1S4_6 IgG light chain is re provided in FIG. 9.

Figures 5A, 5B, 5C:
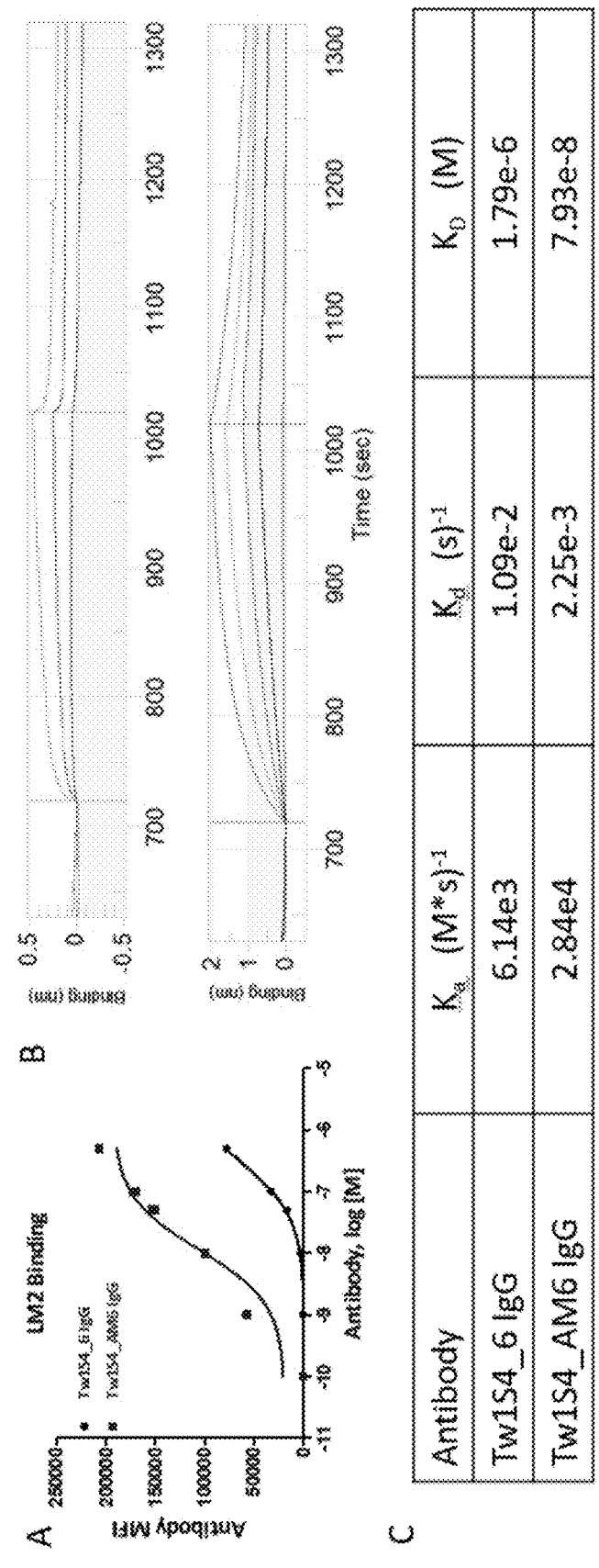
FIGS. 5A-5C: Evaluation of affinity matured antibody Tw1S4_AM6. (A) Flow cytometry-based evaluation of $K_D$ value in MDA-MB-231-LM2 cells (B) Biolayer Inferometry Curves for Tw1S4_6 (Top Panel) at 100 nM (green), 500 nM (pink), 1 μM (yellow) and Tw1S4_AM6 (Bottom Panel) at 10 nM (green), 50 nM (black), 200 nM (pink), 400 nM (dark green). (C) $K_a$, $K_d$, and $K_D$ values obtained from curves generated in (B)

Tw1S4_AM6 demonstrated a substantial improvement in the apparent binding affinity. The apparent $K_D$ estimated from regression analysis of flow cytometry binding curves to LM2 cells was 10 nM, a greater than 10-fold improvement in binding affinity compared to the parent antibody (FIGS. 5A-5C). The parent TwiS4_6 antibody and the optimized Tw1S4_AM6 antibody have identical heavy chains, and therefore CDR 1, 2 and 3 on the heavy chains are identical. The light chains of the parent TwiS4_6 antibody and the optimized Tw1S4_AM6 antibody differ only in CDR 3. Light chain CDR 3 of TwiS4_6 is QQSLRSPIT (SEQ ID NO: 16), whereas Light chain CDR 3 of Tw1S4_AM6 is QQTRNHRTH (SEQ ID NO: 7).

An important caveat with flow cytometry-based titration curves is the potential for avidity affects contributing to the binding, resulting in an 'apparent $K_D$'. Biophysical techniques are most often employed to generate the true, analytically relevant 'intrinsic $K_D$' value. We chose biolayer interferometry as a means of assessing the kinetics of antibody-antigen binding with HSPG2D1. Surprisingly, the parent antibody Tw1S4_6 returned a very modest $K_D$ value in the µM range (FIG. 5C). Affinity matured Tw1S4_AM6 demonstrated substantial monovalent affinity improvement to HSPG2D1, having a $K_D$ value of 80 nM (FIG. 5C).

Tw1S4 Antibodies are Effective in Inhibiting Tumor Growth In Vivo

Figures 6A, 6B, 6C:
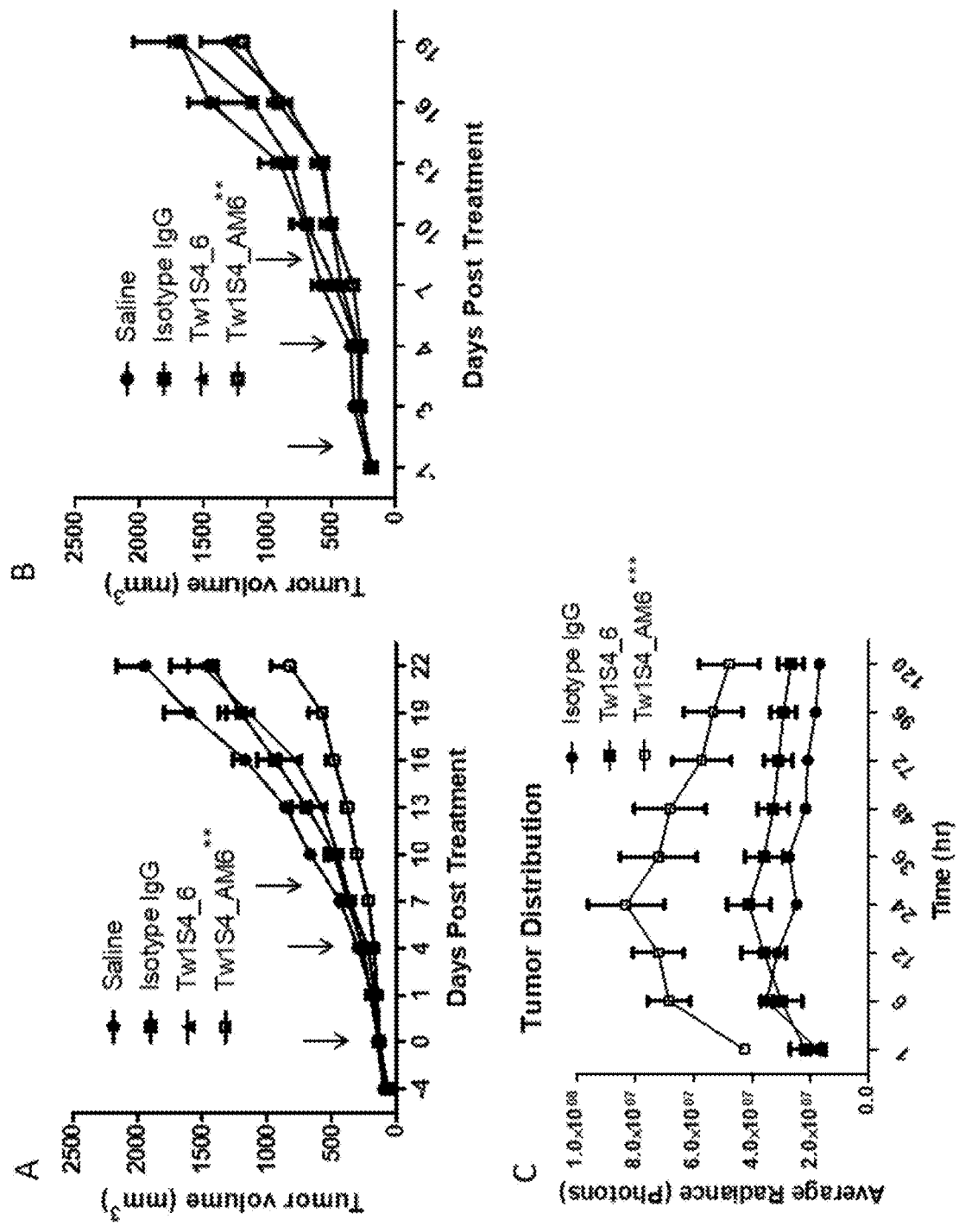
FIGS. 6A-6C: In vivo efficacy and bio-distribution studies for Tw1S4 antibodies. MB-231-LM2 tumors were grafted by subcutaneous injections. For efficacy studies (A and B) dosing begun when the tumors crossed 100 mm$^3$. All antibodies were dosed at 5 mg/kg, 3 doses, every 96 hours (indicated by arrows). (A) Efficacy study in athymic nude mice. Tw1S4_AM6 showed significant tumor inhibition (P<0.01, two-way ANOVA with multiple comparisons, statistical significance is based off comparison between isotype IgG and Tw1S4_AM6 on the last day of the study) (B) Efficacy study in NSG mice. Tw1S4_AM6, although significant, showed blunted efficacy. (P<0.01, two-way ANOVA with multiple comparisons, statistical significance is based off comparison between isotype IgG and Tw1S4_AM6 on the last day of the study) (C) Quantified fluorescence values in tumor. Imaging was done when tumors reached 300 mm$^3$. 100 μg of antibody was injected per mouse. Imaging was carried out at the time points indicated in the figure. Tw1S4_AM6 accumulated between 2-4-fold higher concentrations in the tumor (***P<0.001, two-way ANOVA with multiple comparisons, statistical significance is based off comparison between isotype IgG and Tw1S4_AM6 at 24 hours).

Fully human IgGs are capable of engaging with murine FcγR expressed on various immune effector cells. Balb/c nude mice are athymic yet retain baseline levels of natural killer (NK) cells. This mouse model was initially employed as an in vivo model capable of facilitating ADCC when using human IgG. The original Tw1S4_6 IgG produced marginal tumor growth inhibition relative to the saline treated group (FIG. 6A). The affinity matured variant, Tw1S4_AM6, produced a pronounced inhibition of tumor growth, resulting in a mean tumor volume of 500 mm$^3$ at day 22, relative to saline and isotype control groups, which had mean tumor volumes >1,500 mm$^3$ at the same time point.

To evaluate the specific contribution of immune based effector cells in the mechanism of Tw1S4 antibodies, we used the severely immunocompromised NSG mouse model, which lacks lymphocytes and innate immune cells, including NK cells. An identical graft model in NSG mice led to a statistically significant reduction in tumor volumes at study end-point for Tw1S4_6 and Tw1S4_AM6 (FIG. 6B). The reduction in tumor volumes observed in the NSG mouse model was however blunted, relative to the Balb/c nude model, suggesting a significant contribution of immune based effectors to the efficacy of Tw1S4_AM6. Further experiments are required to understand what drives the residual efficacy observed in NSG mice for both Tw1S4_6 and Tw1S4_AM6.

To understand the reason for differences in the therapeutic efficacy of Tw1S4_6 and Tw1S4_AM6, which differ only in the CDRs, tumor distribution of the two antibodies was investigated. An imaging study was carried out in tumor-bearing mice with fluorescently labeled antibodies. Following IV administration, fluorescence was visible in the liver at one hour. Starting at 12 hours, significant accumulation of the antibodies could be observed in the tumor. Quantitative analysis of fluorescence in the tumors revealed a 2-4 fold higher accumulation of Tw1S4_AM6 versus the isotype IgG control ($P<0.05$ at 6 and 72-120 hrs, $p<0.001$ at 12-48 hrs), similar to other reports (FIG. 6C). TW1S4_6 on the other hand showed a modest, statistically not significant improvement in accumulation (1.5- to 2-fold, $P>0.05$). The $T_{max}$ for both Tw1S4_6 and Tw1S4_AM6 was 24 hours. It is interesting to note that the kinetics of tumor accumulation was very similar in case of TW1S4_6 and Tw1S4_AM6 but was different in the case of isotype IgG. We also analyzed liver accumulation of the antibodies and observed that the $T_{max}$ was the first measured time-point, i.e., 1 hour. There were no differences in the liver distribution of the three antibodies ($P>0.05$).

Tw1S4_AM6 Mediates ADCC In Vitro with Mouse Splenocytes and Human PBMCs

Figures 7A, 7B, 7C, 7D:
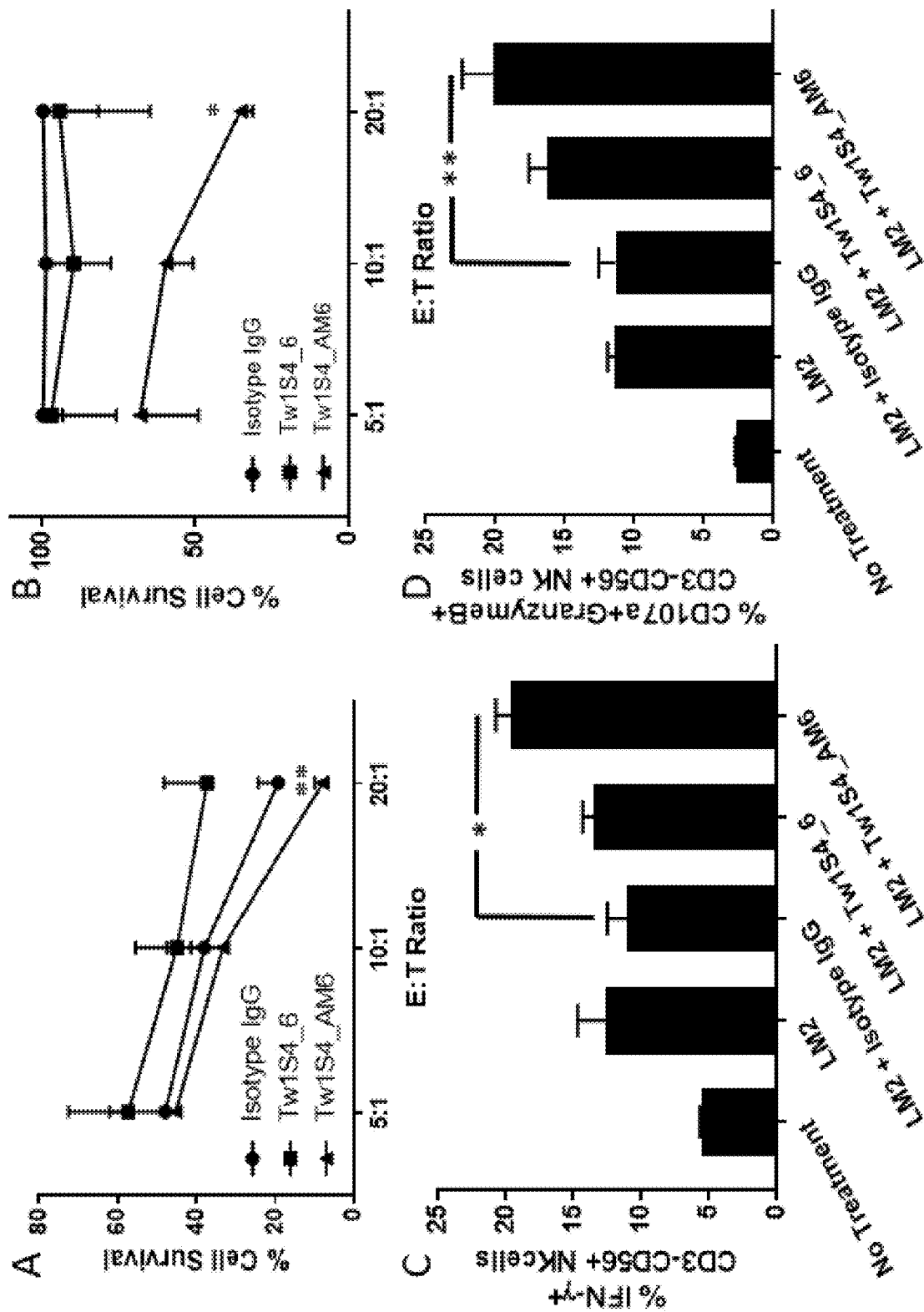
FIGS. 7A-7D: In vitro ADCC assays with Tw1S4 antibodies. (A) ADCC assay with mouse splenocytes showed improved cytotoxicity with Tw1S4_AM6 (**P<0.01, two way ANOVA with Tukey's multiple comparison tests, statistical significance is based off comparison between Tw1S4_6 and Tw1S4_AM6 at E:T 20:1) (B) ADCC assay with human PBMCS from donor 1 showed significantly higher cytotoxicity with Tw1S4_AM6 (*P<0.05, two way ANOVA with Tukey's multiple comparison tests, statistical significance is based off comparison between Isotype IgG and Tw1S4_AM6 at E:T 20:1) (C) and (D) NK cell degranulation assays with human PBMCs from donor 1 (*P<0.05, **P<0.01, one way ANOVA with Tukey's multiple comparison tests).

The observed differences in efficacy in athymic nude v/s NSG mouse models suggested the possible involvement of immune based effector cells in mediating the anticancer efficacy of Tw1S4 antibodies in particular, ADCC. We carried out in vitro ADCC assays with mouse splenocytes. Tw1S4_AM6 induced ADCC resulting in cell survival of 8%, as opposed to 33% with Tw1S4_6 and 19% with Isotype IgG at an effector-to-target (E:T) ratio of 20:1 (FIG. 7A). A similar trend was observed at lower E:T ratios of 10:1 and 5:1. The inclusion of IL2 (as a stimulant) in the assay resulted in high non-specific cell kill. However, previous reports suggested that human antibodies do not show cell lysis with mouse effector cells unless stimulated. It was not surprising that Tw1S4_6 showed no ADCC in vitro considering that antibody affinity has been shown to be a critical parameter in determining ADCC outcome, especially at the low antibody concentrations tested (~0.015 mg/ml). Another possible mechanism exerted by antibodies is complement dependent cytotoxicity. However, we did not observe any cytotoxicity in vitro with either mouse or human serum.

In order to test the translational potential of the TW1S4 antibodies, we also tested in vitro ADCC and NK cell degranulation with healthy human PBMCs from two donors. At an E:T ratio of 20:1, we observed that treatment with Tw1S4_AM6 resulted in a significantly higher tumor cell kill (35% viability as opposed to 99% and 94% in case of Isotype IgG and Tw1S4_6 antibodies, respectively in FIG. 7B), with similar trends at lower ratios. The data from the cell survival-based assay (CFSE in FIG. 7B) correlated well with the cytotoxicity assay. We also observed an increase in the fraction of $CD3^-/CD56^+$ cells secreting Interferon-γ (FIG. 7C), an activation marker (11% for Isotype IgG v/s 19% for Tw1S4_AM6) and those positive for CD107a (FIG. 7D), a degranulation marker (11% for Isotype IgG v/s 20% for Tw1S4_AM6). A similar dataset was obtained with a second donor, however the overall cytotoxicity observed was significantly lower in case of donor 2. This is likely explained by the existence of two isoforms of the FcγIIIa receptor of NK cells involved in ADCC, of which the valine isoform has better binding affinity to the Fc portion of IgG1 s. As a result, patients with the valine isoform are categorized as "high-responders" to antibody immunotherapy.

Discussion

EMT is considered as rate-limiting to cancer dissemination from the primary tumor. The EMT phenotype harbors genes of metastatic aggressiveness that exist transiently in both disseminating cancer cells in the circulation as well as on extravasated cells within early micrometastatic lesions. Uncovering unique EMT cell antigens can lead to new avenues in the therapeutic management of metastasis. A technique well suited for cell surface antigen identification within minority cell populations is phenotype-based screening. When whole cells are used as an antigen source, combinatorial library screens can be designed to identify binders to a relevant cellular phenotype. Screening approaches that employ combinatorial antibody libraries can be designed to identify functional candidate antibodies that bind to a relevant phenotype, capturing the target antigen, as it would exist in its physiologically relevant form. This provides a direct route to antibody drug or diagnostic reagents that could likely be readily translated into therapeutic relevance. Given that prior knowledge of a potential target is not needed, this approach is also highly amenable to novel biomarker discovery via target deconvolution.

A two-antibody set, spanning an order of magnitude in apparent $K_D$ towards cell surface affiliated HSPG2, was developed from phage display-based whole cell phenotype screening. A hard randomization approach for affinity maturation was employed to randomize light chain CDR3 of our initial candidate scFv, Tw1S4_6. Subsequent panning experiments led to the identification of an improved affinity variant, Tw1S4_AM6.

HSPGs are known ubiquitous constituents of extracellular matrix (ECM) and vascular basement membranes. HSPG2 is the primary HSPG within tissue and vascular basement membranes, and has also been observed to be affiliated with the surface of malignant cells, and in tumor stroma. Tumor cells as well as stromal cells, including fibroblasts, endothelial and smooth muscle cells, produce and secrete HSPG2. Functional roles of HSPG2 are diverse, and include participation in the scaffolding function of ECM, along with collagens, laminins and fibronectin. The dramatic shift in HSPG2 localization from the stromal compartment in normal adjacent tissue to the malignant cells in invasive carcinoma as well as the significant increases in HSPG2 expression with tumor stage raises interesting questions related to the role of HSPG2 in carcinoma progression. Previous reports have implicated the involvement of HSPG2 in malignancies including colon carcinoma, prostate cancer, ovarian cancer, Kaposi's sarcoma and lung cancer.

The correlation of high HSPG2 expression with poor patient survival is another indicator of its likely involvement in carcinoma progression. Interestingly, this correlation was observed specifically in case of TNBC patients and not in other subtypes. The absence of correlation in other subtypes could be indicative of HSPG2's involvement in more aggressive and metastatic tumors, such as TNBC. Groups studying HSPG2 in other cancers have also reported similar findings. In pancreatic adenocarcinoma, progressive loss of stromal HSPG2 expression correlates to disease progression. Malignant melanoma cells show upregulated HSPG2 expression relative to non-invasive cells. Downregulation of HSPG2 expression using antisense in colon carcinoma cells resulted in decreased tumor growth and angiogenesis. A similar decrease in proliferation occurred in melanoma and Kaposi's sarcoma cell lines following HSPG2 downregulation using antisense.

Interestingly, Tw1S4_6 antibody also demonstrated binding to CTCs that expressed mesenchymal markers. CTC enumeration has prognostic value in breast cancer. However, it is not currently recommended for use as a molecular marker. CELLSEARCH, the only approved CTC capture platform, is reliant on an antibody directed against EpCAM. Recent studies demonstrate the absence of EpCAM and presence of mesenchymal marker expression in CTC subsets from breast cancer patients. Importantly, dynamic phenotypic changes in CTCs have been observed in response to therapeutic regimen. Patients who responded well to therapy have CTCs with epithelial markers, whereas progressive disease is accompanied by predominately mesenchymal CTCs. Thus, for CTC enumeration and characterization to become an effective tool to inform disease management, mesenchymal-like CTCs must be included and characterized. Currently available markers of EMT are either intracellular or are not specific for cancer cells and thus are not optimal for isolation or characterization of mesenchymal CTCs. Our studies show that Tw1S4_6 is a useful reagent to identify mesenchymal phenotypic CTCs.

Given the success of Trastuzumab and Ado-trastuzumab emtansine conjugate against HER-2 positive breast cancer, there is considerable interest in developing similar antibody-based therapies for TNBC. The in vivo efficacy observed with Tw1S4_AM6 as a single agent treatment points to a potential, exciting new antibody-based therapeutic approach in TNBC. These results also suggest that further refinement of the dosing schedule may be required to achieve durable responses. It is worth noting that antibody dosing of 5 mg/kg is low relative to the doses used for other anti-cancer antibodies. In rodent xenograft models, reported doses range from 10-40 mg/kg for the EGFR targeted antibody cetuximab for at least five doses.

ADCC is an immune effector mechanism mediated primarily by NK cells. Most antibodies (IgG1s) are able to simultaneously engage target-expressing cells through the Fv portion and NK cells through the Fc portion. This leads to activation of NK cells, followed by a release of cytotoxic proteins such as perforin and granzyme, resulting in death of target cells. Antibodies such as trastuzumab and cetuximab, which are primarily known for inhibition of signaling pathways, also show a significant level of ADCC. The ability of Tw1S4_AM6 to mediate cell-kill via ADCC opens up several options to enhance its efficacy. Others were able to map the entire Fc portion of the antibody to identify three amino acid substitutions that led to improvements in ADCC. A variant of Rituximab (KM3065), produced with a reduced core fucosylation, was able to improve ADCC by 1.5-2 fold. Another option is to combine antibodies with NK cell stimulating agents. Such improvements in efficacy could be particularly beneficial to patients with the phenylalanine isoform of FcγRIIIa.

In summary, the cell phenotype-based screening approach outlined here demonstrates the ability to identify cell type specific antigens in the context of mixed phenotype cell populations, a distinct advantage over more conventional target-based screening approaches. The inclusion of the HMLE isogenic cell line pair in the competition screen identified a unique and phenotype-specific epitope within HSPG2. Identification of HSPG2 as a unique tumor cell antigen and development of a fully human antibody demonstrating therapeutic efficacy represent a new point of focus in TNBC.

Example 2

Production of Glycoengineered Antibodies

Figure 16A:
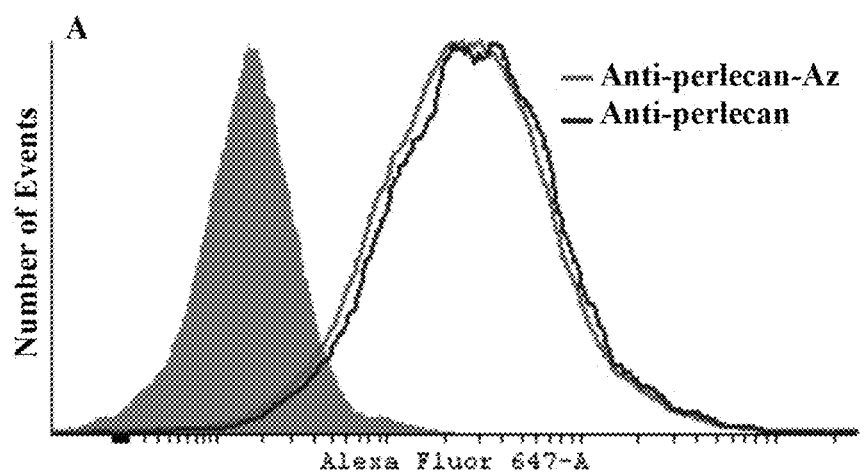
FIGS. 16A-16B. Glycoengineering does not affect binding affinity.
Figure 16B:
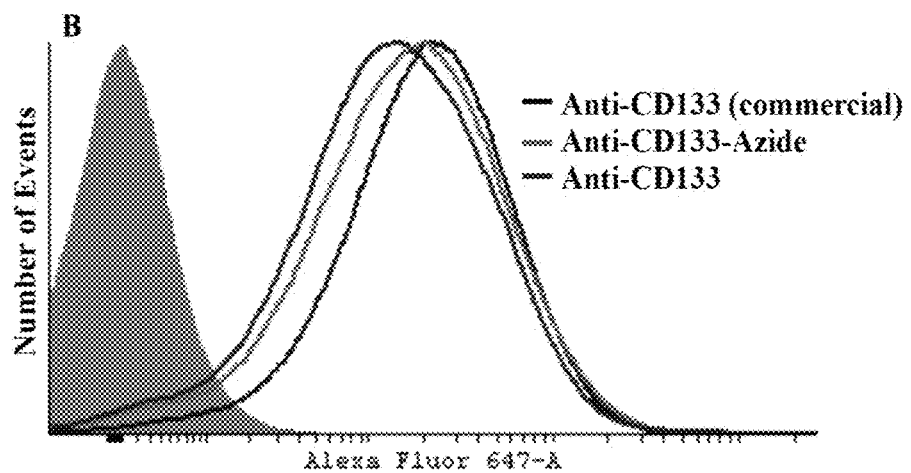
Figure 17:
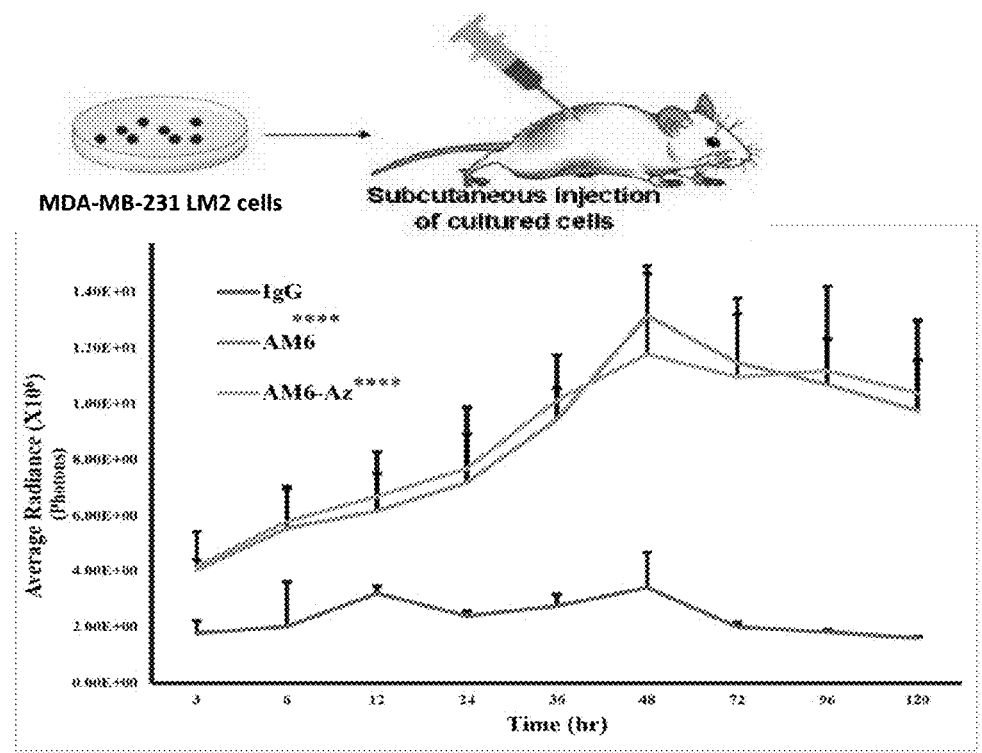
FIG. 17. Glycoengineered antibody accumulates in tumor. Dose: IV injection of 100 μg dye conjugated AM6, AM6-Az and IgG antibody after tumor reaching 300 mm³.

Anti-perlecan-Az (AM60Az) antibodies were produced using a glycoengineering strategy to incorporate azide groups in the N-glycan region of two different antibodies without affecting the antigen binding or in vivo tumor accumulation of the antibody. FIGS. 12, 13, 14A-14B, 15. The glycoengineering did not affect binding affinity. FIG. 16A-16B. The glycoengineered antibody accumulated in tumors. FIG. 17.

Thus, cyclooctyne containing payloads including fluorophores and PEG conjugates were successfully conjugated to glycoengineered antibodies. These results show that the glycoengineering strategy is applicable to synthesize antibody conjugates for therapeutic and diagnostic applications.

Example 3

Glycoengineered Antibody for Synthesis of Antibody Drug Conjugate (ADC)

Figure 18:
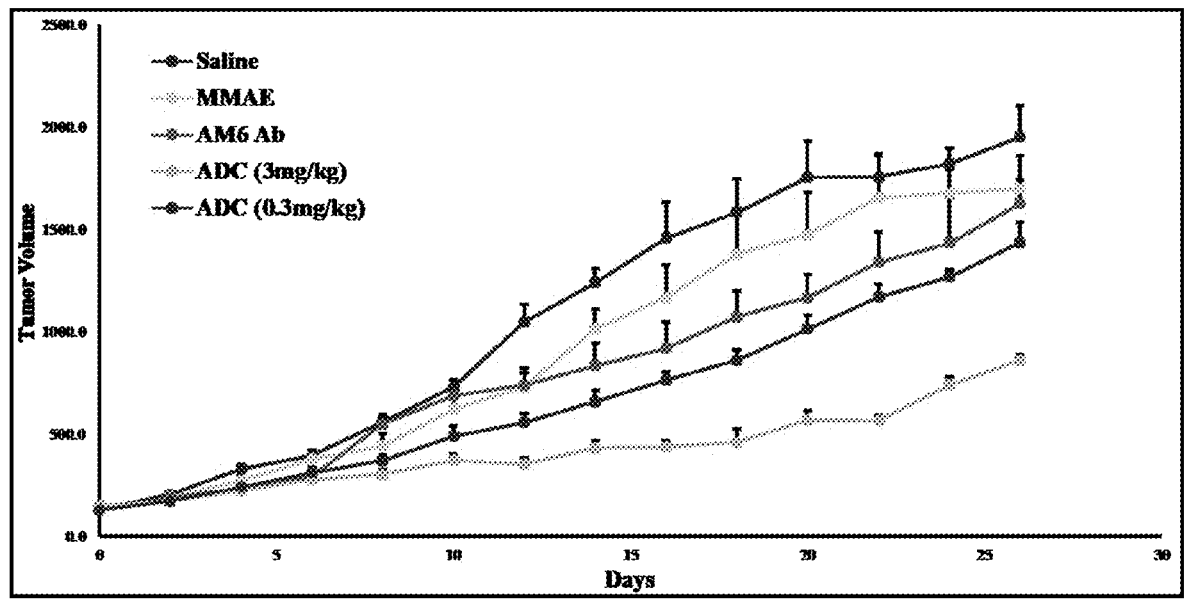
FIG. 18. ADC is effective in inhibiting tumor growth in vivo.

MDA-MB-231 LM2 cells were cultured and the subcutaneously injected into mice. The treatment groups were the following: Saline, MMAE drug, AM6-Az Ab, and ADC. The dosages were the following IV injection of dose equivalent 3 mg/kg or 0.3 mg/kg of antibody at day 0, day 4 and day 8. The results show that that the glycoengineered antibody was effectively internalized and that the ADC was effective in inhibiting tumor growth in vivo (FIG. 18).

The glycoengineered antibody was used to generate AM6-MMAE ADC with a DAR of 2-3 drug molecules per antibody. This ADC showed enhanced antitumor efficacy in vitro as well as in vivo.

Example 4

Figures 19, 20:
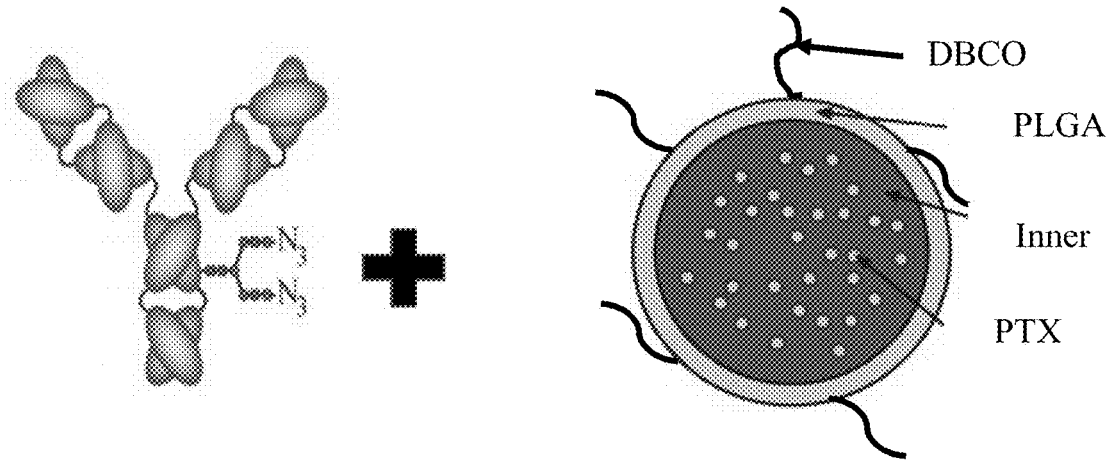
FIG. 19. Formation of antibody conjugated nanoparticles.
FIG. 20. Characterization of antibody conjugated nanoparticles.

Glycoengineered Antibody for Surface Functionalization of Polymeric Nanoparticles Nanoparticles increase the efficacy, safety and tolerability of antibodies. They also enhance permeation and retention in tissue. A schematic of the formation of antibody conjugated nanoparticles is depicted in FIG. 19. Characterization of antibody conjugated nanoparticles is provided in the table of FIG. 20.

An antibody conjugated nanoparticle was produced that targets Triple negative breast cancer (TNBC). Anti-perlecan conjugated nanoparticles (NP) were taken up by MDA-MB-231 LM2 cells (FIG. 21). The in vitro efficacy of anti-perlecan conjugated NP is shown in FIG. 22.

Figure 23:
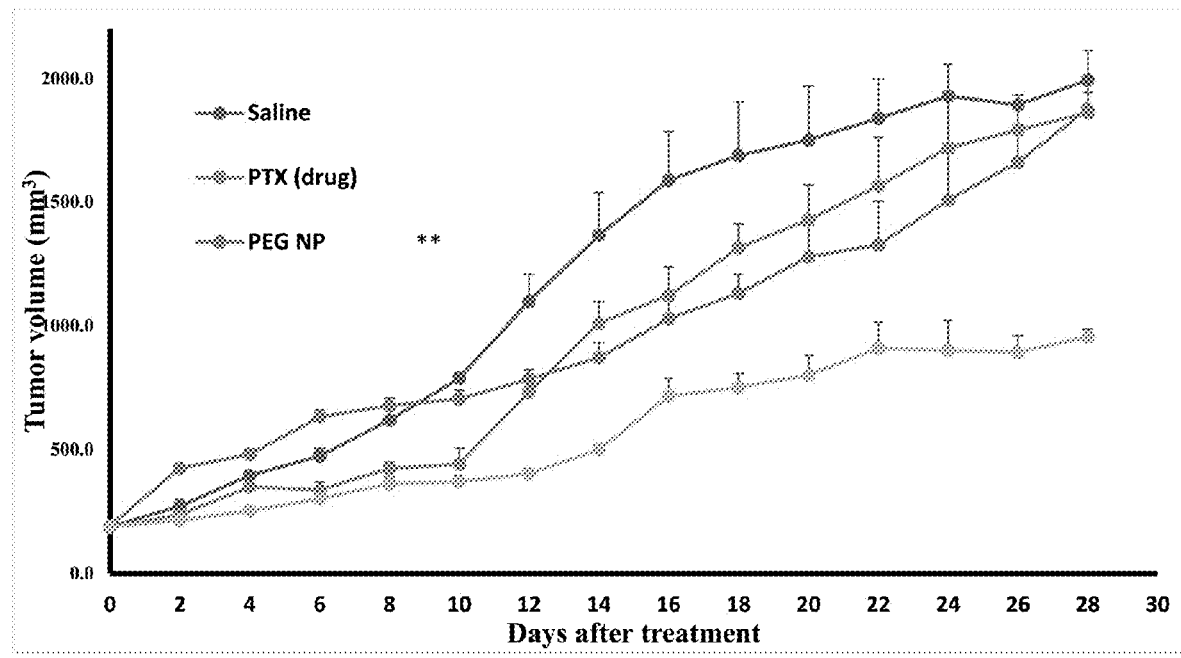
FIG. 23. Antibody conjugated nanoparticles result in improved efficacy.

Efficacy studies were performed with antibody conjugated nanoparticles. MDA-MB-231 LM2 cells were cultured and the subcutaneously injected into mice. Antibody conjugated nanoparticles result in improved efficacy (FIG. 23).

Figure 24:
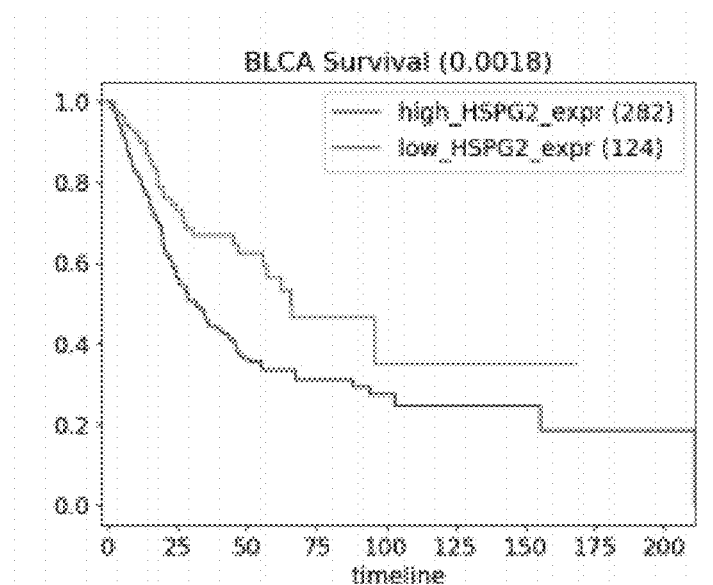
FIG. 24. Antibody conjugated nanoparticle: Bladder cancer.
Figure 25:
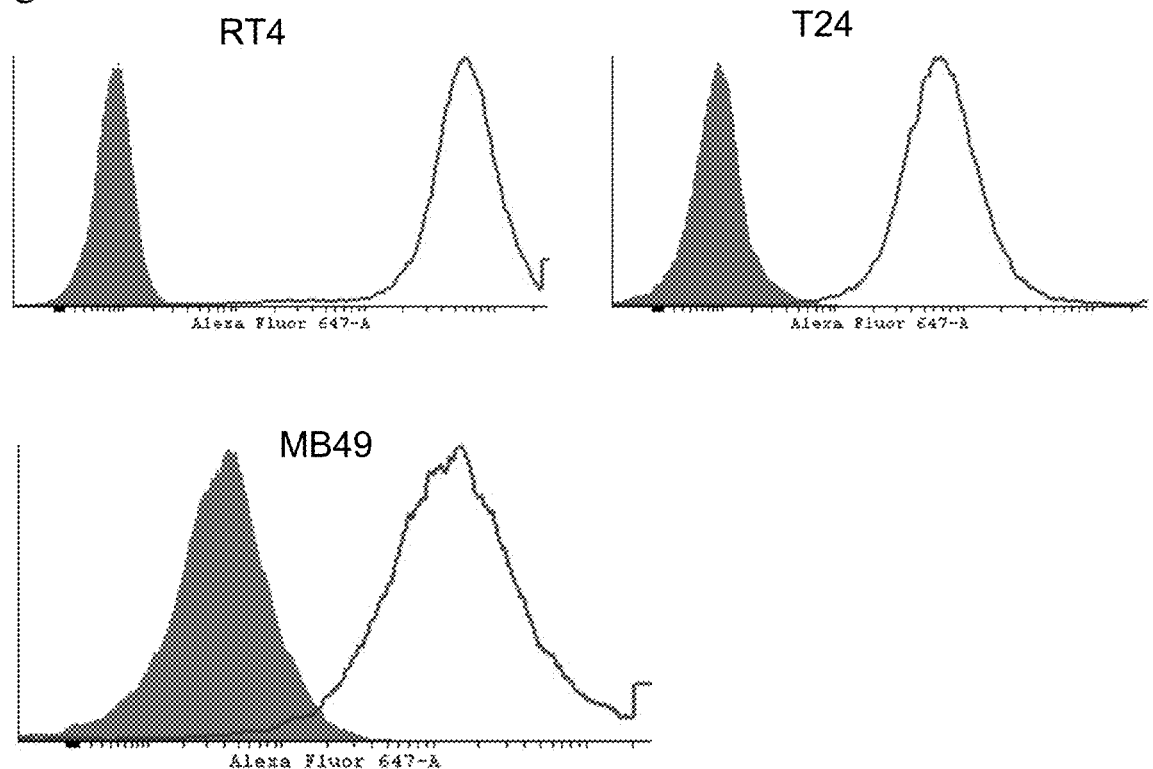
FIG. 25. Anti-perlecan antibody binds to bladder cancer cell lines.

Studies were also performed using antibody conjugated nanoparticle targeting bladder cancer (FIG. 24). The results show that anti-perlecan antibody bound to bladder cancer cell lines (FIG. 25).

Experiments were also performed to study the cell uptake of antibody conjugated nanoparticles (FIG. 26). The results of studies investigating in vitro cytotoxicity with antibody conjugated nanoparticles is provided in FIG. 27.

Figure 28:
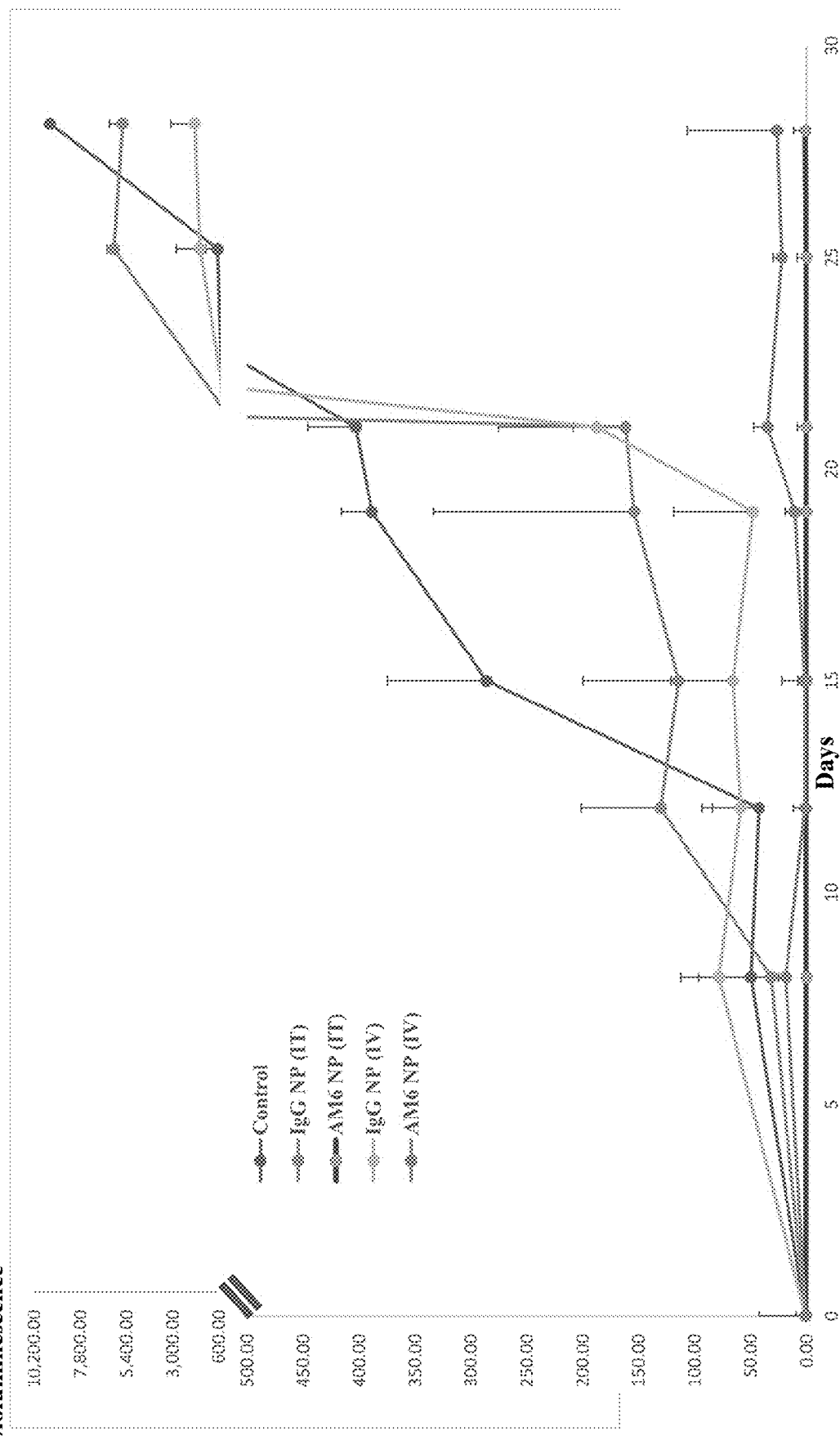
FIG. 28. Tumor growth inhibition with antibody conjugated nanoparticles.

The effects of tumor growth inhibition with antibody conjugated nanoparticles are provided in FIG. 28. Dose: Intravenous (IT) or intratumor (IT) (using urethral catheter) injection of NP, dose equivalent 40 mg/kg PTX at day 0, day 4 and day 8.

In conclusion, glycoengineered AM6 antibody was used to generate perlecan-targeted nanoparticles loaded with paclitaxel. Antibody conjugated nanoparticles showed enhanced antitumor efficacy in vitro as well as in vivo in TNBC models. Targeted nanoparticles also demonstrated enhanced antitumor efficacy in vitro and complete tumor growth inhibition in vivo in a non-muscle invasive bladder cancer model.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated antibody Tw1S4_AM6 or fragment thereof, comprising at least one heavy chain variable region and at least one light chain variable region, wherein the heavy chain variable region comprises heavy chain complementarity-determining regions comprising each of amino acid sequences SEQ ID NOs: 2, 3 and 4, and wherein the light chain variable region comprises light chain complementarity-determining regions comprising each of amino acid sequences SEQ ID NOs: 5, 6 and 7.

2. The isolated antibody Tw1S4_AM6 or fragment of claim 1, wherein the heavy chain variable region is SEQ ID NO: 8.

3. The isolated antibody Tw1S4_AM6 or fragment of claim 1, wherein the light chain variable region is SEQ ID NO: 9.

4. The isolated antibody Tw1S4_AM6 or fragment of claim 1, wherein the heavy chain is SEQ ID NO: 22 or SEQ ID NO: 10.

5. The isolated antibody Tw1S4_AM6 or fragment of claim 1, wherein the light chain is SEQ ID NO: 21 or SEQ ID NO: 11.

6. The isolated antibody Tw1S4_AM6 or fragment of claim 1, wherein the antibody fragment is scFv AM6 (SEQ ID NO: 1).

7. The isolated antibody Tw1S4_AM6 or fragment of claim 1, wherein the antibody is IgG Tw1S4_AM6 comprising two heavy chains, wherein each heavy chain is SEQ ID NO:22 or SEQ ID NO:10 and two light chains, wherein each light chain is SEQ ID NO:21 or SEQ ID NO:11.

8. An immune reagent comprising
(a) a first binding moiety comprising an antibody or antibody fragment of claim 1, and
(b) a second binding moiety comprising antibody or antibody fragment linked to the first antibody or antibody fragment.

9. The immune reagent of claim 8, wherein both the first and the second binding moieties comprise an isolated antibody Tw1S4_AM6 or fragment thereof, comprising at least one heavy chain variable region and at least one light chain variable region, wherein the heavy chain variable region comprises heavy chain complementarity-determining regions comprising each of amino acid sequences of SEQ ID NOs: 2, 3 and 4, and wherein the light chain variable region comprises light chain complementarity-determining regions comprising each of amino acid sequences of SEQ ID NOs: 5, 6 and 7.

10. The immune reagent of claim 9, wherein both the first and second binding moieties comprise scFv AM6 (SEQ ID NO: 1).

11. The immune reagent of claim 9, wherein both the first and second binding moieties comprise IgG Tw1S4_AM6 comprising two heavy chains, wherein each heavy chain is SEQ ID NO:22 or SEQ ID NO:10 and two light chains, wherein each light chain is SEQ ID NO:21 or SEQ ID NO:11.

12. A conjugate comprising the antibody or antibody fragment of claim 1 conjugated to a detection agent or therapeutic agent.

13. The conjugate of claim 12, wherein the immune reagent is conjugated to a detection agent.

14. The conjugate of claim 12, wherein the immune reagent is conjugated to a therapeutic agent.

15. The conjugate of claim 14, wherein the therapeutic agent is selected from trans retinoic acid, Azacitidine, Azathioprine, Bleomycin, Bortezomib, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Mechlorethamine, Mercaptopurine, Methotrexate, Mitoxantrone, Oxaliplatin, Paclitaxel, silicate prodrug of Paclitaxel, Pemetrexed, Teniposide, Tioguanine, Valrubicin, Vinblastine, Vincristine, Vindesine, Vinorelbine, Axitinib, Bosutinib, Cediranib, Dasatinib, Erlotinib, Gefitinib, Imatinib, Lapatinib, Lestaurtinib, Nilotinib, Semaxanib, Sunitinib, Vemurafinib or Vandetanib.

16. A pharmaceutical composition comprising the antibody or antibody fragment of claim 1 and a pharmaceutically acceptable excipient.

17. A composition comprising the antibody or antibody fragment of claim 1 linked to a carrier.

18. The composition of claim 17, wherein the carrier is a nanoparticle or liposome.

19. A method of reducing proliferation or growth of a tumor by administering the antibody or antibody fragment of claim 1 to a patient in need thereof.

\* \* \* \* \*

SEQUENCE LISTING

```
<160> NUMBER OF SEQ ID NOS: 29

<210> SEQ ID NO 1
<211> LENGTH: 241
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Glu Val Gln Leu Leu Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Ser Tyr Ala Met Ser Trp Val Arg Gln Ala Pro Gly Lys Gly Leu Glu
        35                  40                  45

Trp Val Ser Ala Ile Arg Glu Asp Gly Ile Lys Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Arg Ala Arg Arg Phe Asp Tyr Trp Gly Gln Gly Thr
                100                 105                 110

Leu Val Thr Val Leu Ser Gly Gly Gly Ser Gly Gly Gly Gly Ser
            115                 120                 125

Gly Gly Gly Gly Ser Asp Ile Gln Met Thr Gln Ser Pro Ser Ser Leu
```

```
                130                 135                 140
Ser Ala Ser Val Gly Asp Arg Val Thr Ile Thr Cys Arg Ala Ser Gln
145                 150                 155                 160

Ser Ile Ser Ser Tyr Leu Asn Trp Tyr Gln Gln Lys Pro Gly Lys Ala
                165                 170                 175

Pro Lys Leu Leu Ile Tyr Asn Ala Ser Leu Leu Gln Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Thr
    210                 215                 220

Arg Asn His Arg Thr His Phe Gly Gln Gly Thr Lys Val Glu Ile Lys
225                 230                 235                 240

Arg

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Phe Thr Phe Ser Ser Tyr Ala Met Ser
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Ser Ala Ile Arg Glu Asp Gly Ile Lys Thr Tyr Tyr Ala Asp Ser
1               5                   10                  15

Val

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ala Arg Arg Phe Asp Tyr
1               5

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Gln Ser Ile Ser Ser Tyr Leu Asn
1               5                   10
```

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Asn Ala Ser Leu Leu Gln Ser
1               5
```

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

```
Gln Gln Thr Arg Asn His Arg Thr His
1               5
```

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Arg Glu Asp Gly Ile Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ala Arg Arg Phe Asp Tyr Trp Gly Gln Gly Thr Leu Val
            100                 105                 110

Thr Val Ser Ser Ala
        115
```

<210> SEQ ID NO 9
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
```

```
                    20                  25                  30

Tyr Leu Asn Trp Tyr Gln Gln Lys Pro Gly Lys Ala Pro Lys Leu Leu
                35                  40                  45

Ile Tyr Asn Ala Ser Leu Leu Gln Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Thr Arg Asn His Arg
                85                  90                  95

Thr His Phe Gly Gln Gly Thr Lys Val Glu Ile Lys Arg Thr
            100                 105                 110

<210> SEQ ID NO 10
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Tyr Arg Met Gln Leu Leu Ser Cys Ile Ala Leu Ser Leu Ala Leu
1               5                   10                  15

Val Thr Asn Ser Glu Val Gln Leu Leu Glu Ser Gly Gly Gly Leu Val
                20                  25                  30

Gln Pro Gly Gly Ser Leu Arg Leu Ser Cys Ala Ala Ser Gly Phe Thr
            35                  40                  45

Phe Ser Ser Tyr Ala Met Ser Trp Val Arg Gln Ala Pro Gly Lys Gly
        50                  55                  60

Leu Glu Trp Val Ser Ala Ile Arg Glu Asp Gly Ile Lys Thr Tyr Tyr
65                  70                  75                  80

Ala Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
            100                 105                 110

Val Tyr Tyr Cys Ala Lys Arg Ala Arg Arg Phe Asp Tyr Trp Gly Gln
        115                 120                 125

Gly Thr Leu Val Thr Val Ser Ser Ala Ser Thr Lys Gly Pro Ser Val
130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
210                 215                 220

Pro Ser Asn Thr Lys Val Asp Lys Lys Val Glu Pro Lys Ser Cys Asp
225                 230                 235                 240

Lys Thr His Thr Cys Pro Pro Cys Pro Ala Pro Glu Leu Leu Gly Gly
                245                 250                 255

Pro Ser Val Phe Leu Phe Pro Pro Lys Pro Lys Asp Thr Leu Met Ile
            260                 265                 270
```

```
Ser Arg Thr Pro Glu Val Thr Cys Val Val Asp Val Ser His Glu
        275                 280                 285

Asp Pro Glu Val Lys Phe Asn Trp Tyr Val Asp Gly Val Glu Val His
290                 295                 300

Asn Ala Lys Thr Lys Pro Arg Glu Glu Gln Tyr Asn Ser Thr Tyr Arg
305                 310                 315                 320

Val Val Ser Val Leu Thr Val Leu His Gln Asp Trp Leu Asn Gly Lys
            325                 330                 335

Glu Tyr Lys Cys Lys Val Ser Asn Lys Ala Leu Pro Ala Pro Ile Glu
        340                 345                 350

Lys Thr Ile Ser Lys Ala Lys Gly Gln Pro Arg Glu Pro Gln Val Tyr
    355                 360                 365

Thr Leu Pro Pro Ser Arg Glu Glu Met Thr Lys Asn Gln Val Ser Leu
370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Val
            405                 410                 415

Leu Asp Ser Asp Gly Ser Phe Phe Leu Tyr Ser Lys Leu Thr Val Asp
        420                 425                 430

Lys Ser Arg Trp Gln Gln Gly Asn Val Phe Ser Cys Ser Val Met His
    435                 440                 445

Glu Ala Leu His Asn His Tyr Thr Gln Lys Ser Leu Ser Leu Ser Pro
        450                 455                 460

Gly Lys
465

<210> SEQ ID NO 11
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Tyr Arg Met Gln Leu Leu Ser Cys Ile Ala Leu Ser Leu Ala Leu
1               5                   10                  15

Val Thr Asn Ser Thr Asp Ile Gln Met Thr Gln Ser Pro Ser Ser Leu
            20                  25                  30

Ser Ala Ser Val Gly Asp Arg Val Thr Ile Thr Cys Arg Ala Ser Gln
        35                  40                  45

Ser Ile Ser Ser Tyr Leu Asn Trp Tyr Gln Gln Lys Pro Gly Lys Ala
    50                  55                  60

Pro Lys Leu Leu Ile Tyr Asn Ala Ser Leu Leu Gln Ser Gly Val Pro
65                  70                  75                  80

Ser Arg Phe Ser Gly Ser Gly Ser Gly Thr Asp Phe Thr Leu Thr Ile
            85                  90                  95

Ser Ser Leu Gln Pro Glu Asp Phe Ala Thr Tyr Tyr Cys Gln Gln Thr
        100                 105                 110

Arg Asn His Arg Thr His Phe Gly Gln Gly Thr Lys Val Glu Ile Lys
    115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160
```

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 12
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atgtacagga tgcaactcct gtcttgcatt gcactaagtc ttgcacttgt cacgaattca      60
gaggtgcagc tgttggagtc tgggggaggc ttggtacagc ctgggggtc cctgagactc     120 tcctgtgcag cctctggatt caccttagc agctatgcca tgagctgggt ccgccaggct     180
ccagggaagg ggctggagtg ggtctcagcg attaggagg atggtattaa gacatattac     240
gcagactccg tgaagggccg gttcaccatc tccagagaca attccaagaa cacgctgtat     300
ctgcaaatga acagcctgag agccgaggac acggccgtat attactgtgc gaaaagggct     360
cgtcggtttg actactgggg ccagggaacc ctggtcaccg tctcgagcgc tagcaccaag     420
ggcccatcgg tcttcccct ggcaccctcc tccaagagca cctctggggg cacagcggcc     480
ctgggctgcc tggtcaagga ctacttcccc gaaccggtga cggtgtcgtg gaactcaggc     540
gccctgacca gcggcgtgca caccttcccg gctgtcctac agtcctcagg actctactcc     600
ctcagcagcg tggtgaccgt gccctccagc agcttgggca cccagaccta catctgcaac     660
gtgaatcaca agcccagcaa caccaaggtg gacaagaaag ttgagcccaa atcttgtgac     720
aaaactcaca catgcccacc gtgcccagca cctgaactcc tggggggacc gtcagtcttc     780
ctcttccccc caaaacccaa ggacaccctc atgatctccc ggacccctga ggtcacatgc     840
gtggtggtgg acgtgagcca cgaagaccct gaggtcaagt tcaactggta cgtggacggc     900
gtggaggtgc ataatgccaa gacaaagccg cgggaggagc agtacaacag cacgtaccgt     960
gtggtcagcg tcctcaccgt cctgcaccag gactggctga atggcaagga gtacaagtgc    1020
aaggtctcca acaaagccct cccagccccc atcgagaaaa ccatctccaa agccaaaggg    1080
cagccccgag aaccacaggt gtacaccctg cccccatccc gggaggagat gaccaagaac    1140
caggtcagcc tgacctgcct ggtcaaaggc ttctatccca gcgacatcgc cgtggagtgg    1200
gagagcaatg ggcagccgga gaacaactac aagaccacgc ctcccgtgct ggactccgac    1260
ggctccttct tcctctacag caagctcacc gtggacaaga gcaggtggca gcaggggaac    1320
gtcttctcat gctccgtgat gcatgaggct ctgcacaacc actacacgca gaagagcctc    1380
tccctgtctc cgggtaaatg a                                              1401

<210> SEQ ID NO 13
<211> LENGTH: 708
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 13

```
atgtacagga tgcaactcct gtcttgcatt gcactaagtc ttgcacttgt cacgaattca    60
acggacatcc agatgaccca gtctccatcc tccctgtctg catctgtagg agacagagtc   120
accatcactt gccgggcaag tcagagcatt agcagctatt taaattggta tcagcagaaa   180
ccagggaaag cccctaagct cctgatctat aatgcatccc ttttgcaaag tggggtccca   240
tcaaggttca gtggcagtgg atctgggaca gatttcactc tcaccatcag cagtctgcaa   300
cctgaagatt ttgcaactta ctactgtcaa cagacccgga atcaccgcac ccacttcggc   360
caagggacca aggtggaaat caaacggacg gtggctgcac catctgtctt catcttcccg   420
ccatctgatg agcagttgaa atctggaact gcctctgttg tgtgcctgct gaataacttc   480
tatcccagag aggccaaagt acagtggaag gtggataacg ccctccaatc gggtaactcc   540
caggagagtg tcacagagca ggacagcaag gacagcacct acagcctcag cagcaccctg   600
acgctgagca aagcagacta cgagaaacac aaagtctacg cctgcgaagt cacccatcag   660
ggcctgagct cgcccgtcac aaagagcttc aacaggggag agtgttag              708
```

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Met Tyr Arg Met Gln Leu Leu Ser Cys Ile Ala Leu Ser Leu Ala Leu
1               5                   10                  15

Val Thr Asn Ser
            20
```

<210> SEQ ID NO 15
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
            20                  25                  30

Pro Glu Pro Val Thr Val Ser Trp Asn Ser Gly Ala Leu Thr Ser Gly
        35                  40                  45

Val His Thr Phe Pro Ala Val Leu Gln Ser Ser Gly Leu Tyr Ser Leu
    50                  55                  60

Ser Ser Val Val Thr Val Pro Ser Ser Leu Gly Thr Gln Thr Tyr
65                  70                  75                  80

Ile Cys Asn Val Asn His Lys Pro Ser Asn Thr Lys Val Asp Lys Lys
                85                  90                  95

Val Glu Pro Lys Ser Cys Asp Lys Thr His Thr Cys Pro Pro Cys Pro
            100                 105                 110
```

```
Ala Pro Glu Leu Leu Gly Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ala Pro Ile Glu Lys Thr Ile Ser Lys Ala Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Ser Leu Arg Ser Pro Ile Thr
1               5

<210> SEQ ID NO 17
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
            20                  25                  30

Arg Glu Ala Lys Val Gln Trp Lys Val Asp Asn Ala Leu Gln Ser Gly
        35                  40                  45

Asn Ser Gln Glu Ser Val Thr Glu Gln Asp Ser Lys Asp Ser Thr Tyr
    50                  55                  60
```

Ser Leu Ser Ser Thr Leu Thr Leu Ser Lys Ala Asp Tyr Glu Lys His
 65                  70                  75                  80

Lys Val Tyr Ala Cys Glu Val Thr His Gln Gly Leu Ser Ser Pro Val
                 85                  90                  95

Thr Lys Ser Phe Asn Arg Gly Glu Cys
            100                 105

<210> SEQ ID NO 18
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
atgtacagga tgcaactcct gtcttgcatt gcactaagtc ttgcacttgt cacgaattca     60
acggacatcc agatgaccca gtctccatcc tccctgtctg catctgtagg agacagagtc    120
accatcactt gccgggcaag tcagagcatt agcagctatt taaattggta tcagcagaaa    180
ccagggaaag cccctaagct cctgatctat aatgcatccc ttttgcaaag tggggtccca    240
tcaaggttca gtggcagtgg atctgggaca gatttcactc tcaccatcag cagtctgcaa    300
cctgaagatt ttgcaactta ctactgtcaa cagagtctgc gttcgcctat tacgttcggc    360
caagggacca aggtggaaat caaacggacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca aagcagacta cgagaaacac aaagtctacg cctgcgaagt cacccatcag    660
ggcctgagct cgcccgtcac aaagagcttc aacaggggag agtgttag                708

<210> SEQ ID NO 19
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Met Tyr Arg Met Gln Leu Leu Ser Cys Ile Ala Leu Ser Leu Ala Leu
  1               5                  10                  15

Val Thr Asn Ser Thr Asp Ile Gln Met Thr Gln Ser Pro Ser Ser Leu
                 20                  25                  30

Ser Ala Ser Val Gly Asp Arg Val Thr Ile Thr Cys Arg Ala Ser Gln
             35                  40                  45

Ser Ile Ser Ser Tyr Leu Asn Trp Tyr Gln Gln Lys Pro Gly Lys Ala
         50                  55                  60

Pro Lys Leu Leu Ile Tyr Asn Ala Ser Leu Leu Gln Ser Gly Val Pro
 65                  70                  75                  80

Ser Arg Phe Ser Gly Ser Gly Ser Gly Thr Asp Phe Thr Leu Thr Ile
                 85                  90                  95

Ser Ser Leu Gln Pro Glu Asp Phe Ala Thr Tyr Tyr Cys Gln Gln Ser
            100                 105                 110

Leu Arg Ser Pro Ile Thr Phe Gly Gln Gly Thr Lys Val Glu Ile Lys
        115                 120                 125

Arg Thr Val Ala Ala Pro Ser Val Phe Ile Phe Pro Pro Ser Asp Glu
            130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 20
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Asn Ala Ser Leu Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Leu Arg Ser Pro
                85                  90                  95

Ile Thr Phe Gly Gln Gly Thr Lys Val Glu Ile Lys Arg Thr
            100                 105                 110

<210> SEQ ID NO 21
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Asn Ala Ser Leu Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

```
Pro Glu Asp Phe Ala Thr Tyr Tyr Cys Gln Gln Thr Arg Asn His Arg
                85                  90                  95

Thr His Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 22
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Arg Glu Asp Gly Ile Lys Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Ala Arg Arg Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
```

```
            210                 215                 220
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 23
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Thr Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Ser Ile Ser Ser
            20                  25                  30

Tyr Leu Asn Trp Tyr Gln Gln Lys Pro Gly Lys Ala Pro Lys Leu Leu
        35                  40                  45

Ile Tyr Asn Ala Ser Leu Leu Gln Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Ser Leu Arg Ser Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125
```

```
Gly Thr Ala Ser Val Val Cys Leu Leu Asn Asn Phe Tyr Pro Arg Glu
130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Glu Ala Ser Gly Gly Pro Glu
1               5

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gaagcttccg gaggtcccga g                                           21

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ccgtctggtc aggctggtgc tgctgctagc gaatctctgt tcgtttctaa ccacgcttac   60

<210> SEQ ID NO 27
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
atggacgagg tgcagctgtt ggagtctggg ggaggcttgg tacagcctgg ggggtccctg   60
agactctcct gtgcagcctc tggattcacc tttagcagct atgccatgag ctgggtccgc  120
caggctccag ggaaggggct ggagtgggtc tcagcgatta gggaggatgg tattaagaca  180
tattacgcag actccgtgaa gggccggttc accatctcca gagacaattc caagaacacg  240
ctgtatctgc aaatgaacag cctgagagcc gaggacacgg ccgtatatta ctgtgcgaaa  300
```

```
agggctcgtc ggtttgacta ctggggccag ggaaccctgg tcaccgtctt gagcggtgga    360
ggcggttcag gcggaggtgg cagcggcggt ggcgggtcgg acatccagat gacccagtct    420
ccatcctccc tgtctgcatc tgtaggagac agagtcacca tcacttgccg ggcaagtcag    480
agcattagca gctatttaaa ttggtatcag cagaaaccag ggaaagcccc taagctcctg    540
atctataatg catccctttt gcaaagtggg gtcccatcaa ggttcagtgg cagtggatct    600
gggacagatt tcactctcac catcagcagt ctgcaacctg aagattttgc aacttactac    660
tgtcaacaga cccggaatca ccgcacccac ttcggccaag gaccaaggt ggaaatcaaa     720 cgg                                                                 723

<210> SEQ ID NO 28
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
tgatagctcg ag                                                        12

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 29

His His His His His His
1               5
```